United States Patent
Dykstra et al.

(10) Patent No.: US 7,543,645 B2
(45) Date of Patent: *Jun. 9, 2009

(54) METHOD FOR SERVICING A WELL BORE USING A MIXING CONTROL SYSTEM

(75) Inventors: Jason D. Dykstra, Duncan, OK (US); Justin A. Borgstadt, Duncan, OK (US)

(73) Assignee: Halliburton Energy Services, Inc., Duncan, OK (US)

(*) Notice: Subject to any disclaimer, the term of this patent is extended or adjusted under 35 U.S.C. 154(b) by 0 days.

This patent is subject to a terminal disclaimer.

(21) Appl. No.: 12/054,211

(22) Filed: Mar. 24, 2008

(65) Prior Publication Data
US 2008/0164023 A1   Jul. 10, 2008

Related U.S. Application Data

(63) Continuation of application No. 11/121,325, filed on May 3, 2005, now Pat. No. 7,353,874.

(60) Provisional application No. 60/671,392, filed on Apr. 14, 2005.

(51) Int. Cl.
*E21B 43/00* (2006.01)
(52) U.S. Cl. ............. 166/305.1; 166/379; 166/385; 366/152.1; 700/285; 137/88
(58) Field of Classification Search ............. 166/305.1, 166/379, 285; 366/8, 17, 152.1; 700/285; 137/3, 88, 91
See application file for complete search history.

(56) References Cited

U.S. PATENT DOCUMENTS

| | | | |
|---|---|---|---|
| 3,379,421 A | 4/1968 | Putman | |
| 3,591,147 A * | 7/1971 | Anderson et al. | 366/142 |
| 3,605,775 A | 9/1971 | Zaander et al. | |
| 3,886,065 A | 5/1975 | Kappe et al. | |
| 3,933,041 A | 1/1976 | Hyer | |
| 4,141,656 A | 2/1979 | Mian | |
| 4,327,759 A | 5/1982 | Millis | |

(Continued)

FOREIGN PATENT DOCUMENTS

EP    0495098 A1    7/1992

(Continued)

OTHER PUBLICATIONS

Advisory Action dated Aug. 7, 2007 (3 pages), U.S. Appl. No. 11/121,144, filed May 3, 2005.

(Continued)

*Primary Examiner*—David J Bagnell
*Assistant Examiner*—Nicole Coy
(74) *Attorney, Agent, or Firm*—John W. Wustenberg; Conley Rose, P.C.

(57) ABSTRACT

A method for servicing a well bore comprises connecting a mixing system to the well bore, controlling the mixing system to produce a material mixture with approximately a desired density, and controlling the mixing system to provide the material mixture to the well bore at approximately a desired volumetric flow rate to service the well bore, wherein the controlling to produce approximately a desired density is independent from the controlling to provide approximately a desired volumetric flow rate.

28 Claims, 18 Drawing Sheets

U.S. PATENT DOCUMENTS

| | | | |
|---|---|---|---|
| 4,349,435 A | 9/1982 | Ochiai | |
| 4,397,561 A | 8/1983 | Strong et al. | |
| 4,421,716 A | 12/1983 | Hench et al. | |
| 4,436,431 A | 3/1984 | Strong et al. | |
| 4,654,802 A | 3/1987 | Davis | |
| 4,764,019 A | 8/1988 | Kaminski et al. | |
| 4,779,186 A | 10/1988 | Handke et al. | |
| 5,027,267 A | 6/1991 | Pitts et al. | |
| 5,038,611 A | 8/1991 | Weldon et al. | |
| 5,098,667 A | 3/1992 | Young et al. | |
| 5,103,908 A | 4/1992 | Allen | |
| 5,114,239 A | 5/1992 | Allen | |
| 5,281,023 A | 1/1994 | Cedillo et al. | |
| 5,289,877 A * | 3/1994 | Naegele et al. | 166/285 |
| 5,320,425 A | 6/1994 | Stephenson et al. | |
| 5,365,435 A * | 11/1994 | Stephenson | 700/265 |
| 5,382,411 A | 1/1995 | Allen | |
| 5,441,340 A | 8/1995 | Cedillo et al. | |
| 5,452,954 A | 9/1995 | Handke et al. | |
| 5,503,473 A | 4/1996 | Dearing, Sr. et al. | |
| 5,570,743 A | 11/1996 | Padgett et al. | |
| 5,571,281 A | 11/1996 | Allen | |
| 5,590,958 A | 1/1997 | Dearing, Sr. et al. | |
| 5,624,182 A | 4/1997 | Dearing, Sr. et al. | |
| 5,775,803 A | 7/1998 | Montgomery et al. | |
| 6,007,227 A | 12/1999 | Carlson | |
| 6,113,256 A | 9/2000 | Bonissone et al. | |
| 6,120,172 A | 9/2000 | Chen et al. | |
| 6,120,173 A | 9/2000 | Bonissone et al. | |
| 6,253,607 B1 | 7/2001 | Dau | |
| 6,491,421 B2 | 12/2002 | Rondeau et al. | |
| 6,505,519 B2 * | 1/2003 | Henry et al. | 73/861.356 |
| 6,786,629 B2 | 9/2004 | Rondeau et al. | |
| 6,932,169 B2 | 8/2005 | Wylie et al. | |
| 7,056,008 B2 | 6/2006 | Rondeau et al. | |
| 7,284,898 B2 | 10/2007 | Duell et al. | |
| 7,308,379 B2 | 12/2007 | Dykstra et al. | |
| 7,353,874 B2 | 4/2008 | Dykstra et al. | |
| 7,356,427 B2 | 4/2008 | Dykstra et al. | |
| 2003/0161211 A1 | 8/2003 | Duell et al. | |
| 2005/0135185 A1 | 6/2005 | Duell et al. | |
| 2006/0141107 A1 | 6/2006 | Schwimmer et al. | |
| 2006/0233039 A1 | 10/2006 | Dykstra et al. | |
| 2007/0153622 A1 | 7/2007 | Dykstra et al. | |
| 2007/0153623 A1 | 7/2007 | Dykstra et al. | |
| 2007/0153624 A1 | 7/2007 | Dykstra et al. | |
| 2007/0171765 A1 | 7/2007 | Dykstra et al. | |

FOREIGN PATENT DOCUMENTS

| | | | |
|---|---|---|---|
| EP | 1356188 B1 | 10/2003 | |
| WO | 9519221 A2 | 7/1995 | |
| WO | 9519221 A3 | 7/1995 | |
| WO | 0236929 A1 | 5/2002 | |
| WO | 0244517 A1 | 6/2002 | |
| WO | 03065015 A1 | 8/2003 | |

OTHER PUBLICATIONS

Advisory Action dated Oct. 1, 2007 (3 pages), U.S. Appl. No. 11/029,072, filed Jan. 4, 2005.

Foreign communication from a related counterpart application—International Search Report and Written Opinion, PCT/GB2006/001307, Jul. 13, 2006, 10 pages.

Foreign communication from a related counterpart application—International Search Report and Written Opinion, PCT/GB2006/001302, Jul. 17, 2006, 14 pages.

Foreign communication from a related counterpart application—Invitation to Pay Additional Fees, PCT/GB2006/000025, Jul. 24, 2006, 5 pages.

Foreign communication from a related counterpart application—International Search Report and Written Opinion, PCT/GB2006/001338, Aug. 3, 2006, 12 pages.

Foreign communication from a related counterpart application—International Search Report and Written Opinion, PCT/GB2006/000025, Oct. 11, 2006, 17 pages.

Kanagasabapathy, P., et al.,"Neural network with reinforcement learning for adaptive time-optimal control of tank level," XP009072551, pp. 17-47, Anna University, Chennai, India.

Notice of Allowance dated Oct. 1, 2007 (13 pages), U.S. Appl. No. 11/121,144, filed May 3, 2005.

Notice of Allowance dated Nov. 6, 2007 (7 pages), U.S. Appl. No. 11/029,072, filed Jan. 4, 2005.

Notice of Allowance dated Jan. 29, 2008 (5 pages), U.S. Appl. No. 11/121,325, filed May 3, 2005.

Notice of Allowance dated Oct. 14, 2008 (6 pages), U.S. Appl. No. 11/121,278, filed May 3, 2005.

Office Action dated Aug. 22, 2006 (8 pages), U.S. Appl. No. 11/029,072, filed Jan. 4, 2005.

Office Action dated Jan. 8, 2007 (16 pages), U.S. Appl. No. 11/029,072, filed Jan. 4, 2005.

Office Action dated Feb. 13, 2007 (21 pages), U.S. Appl. No. 11/121,144, filed May 3, 2005.

Office Action (Final) dated Jun. 8, 2007 (13 pages), U.S. Appl. No. 11/121,144, filed May 3, 2005.

Office Action (Final) dated Jun. 14, 2007 (11 pages), U.S. Appl. No. 11/029,072, filed Jan. 4, 2005.

Office Action dated Jul. 3, 2007 (18 pages), U.S. Appl. No. 11/121,325, filed May 3, 2005.

Office Action (Final) dated Nov. 13, 2007 (10 pages), U.S. Appl. No. 11/121,325, filed May 3, 2005.

Office Action dated May 29, 2008 (27 pages), U.S. Appl. No. 11/121,278, filed May 3, 2005.

Pan, Haizhou, et al., "Experimental validation of a nonlinear backstepping liquid level controller for a state coupled two tank system," Control Engineering Practice, 2005, pp. 27-40, vol. 13, Elsevier Ltd.

Tylee, J. Louis, "Educational uses of microcomputers in control systems design and analysis," Proceedings of the Conference on Modeling and Simulation on Microcomputers, Jan. 14-16, 1987, pp. 132-136, 1 cover page, and 1 publication page, A Society for Computer Simulation (Simulation Councils, Inc.), San Diego, California.

* cited by examiner

METHOD FOR SERVICING A WELL BORE USING A MIXING CONTROL SYSTEM

CROSS-REFERENCE TO RELATED APPLICATIONS

This is a Continuation Application claiming priority to U.S. patent application Ser. No. 11/121,325, filed May 3, 2005 and entitled "Method for Servicing a Well Bore Using a Mixing Control System," which claims priority to U.S. Provisional Application Ser. No. 60/671,392 filed Apr. 14, 2005 and entitled "Implementation of Alternative Cement Mixing Control Schemes," by Jason D. Dykstra, et al. Each of the above patent applications is incorporated herein by reference for all purposes.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

The present disclosure is directed to a mixing process, and more particularly, but not by way of limitation, to a method of servicing a well bore using a mixing control system.

BACKGROUND OF THE INVENTION

A control system typically comprises one or more physical system components under some form of automated control that cooperate to achieve a set of common objectives. The control system may be designed to reliably control the physical system components in the presence of external disturbances, variations among physical components due to manufacturing tolerances, and changes in commanded input values for controlled output values, such as a cement mixture density, for example. The control system may also be designed to remain stable and avoid oscillations within a range of specific operating conditions.

In a well bore environment, a control system may be used when mixing materials to achieve a desired mixture output. For example, when drilling an oil or gas well, it is common to install a tubular casing into the well bore and cement the casing in place against the well bore wall. A cement mixing system that supports well bore servicing operations, such as cementing casing into a well bore, may be designed with a control system configured to provide a desired volumetric flow rate of mixed cement having a desired density. In particular, the cement mixing control system may control valves that allow the in-flow of dry cement material and water to obtain the desired cement mixture density and desired cement mixture volumetric flow rate. The control system may operate, for example, by monitoring the cement mixture flow rate and density, and by regulating an in-flow water valve and an in-flow dry cement material valve. However, because such systems conventionally control the output parameters, such as cement mixture flow rate and density, dependently, these systems tend to have long lag times in the response of one valve to changes in the position of the other valve. This can lead to unacceptable oscillations in the monitored parameters, and difficulty in stabilizing the system. Therefore, to make the system more stable, it would be desirable to control output parameters, such as a mixture flow rate and a mixture density, for example, independently of each other. Accordingly, a need exists for a mixing control system with multiple inputs that decouples the effects of changes in the commanded outputs.

SUMMARY OF THE INVENTION

Disclosed herein is a method for servicing a well bore comprising connecting a mixing system to the well bore, controlling the mixing system to produce a material mixture with approximately a desired density, and controlling the mixing system to provide the material mixture to the well bore at approximately a desired volumetric flow rate to service the well bore, wherein the controlling to produce approximately a desired density is independent from the controlling to provide approximately a desired volumetric flow rate.

These and other features and advantages will be more clearly understood from the following detailed description taken in conjunction with the accompanying drawings and claims.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

DETAILED DESCRIPTION

It should be understood at the outset that the present disclosure describes various implementations of different embodiments of a control system having one or more inputs. However, the present control system may also be implemented using any number of other techniques, whether currently known or in existence. The present disclosure should in no way be limited to the descriptions, drawings, and techniques illustrated below, including the design and implementation illustrated and described herein.

Figure 1:
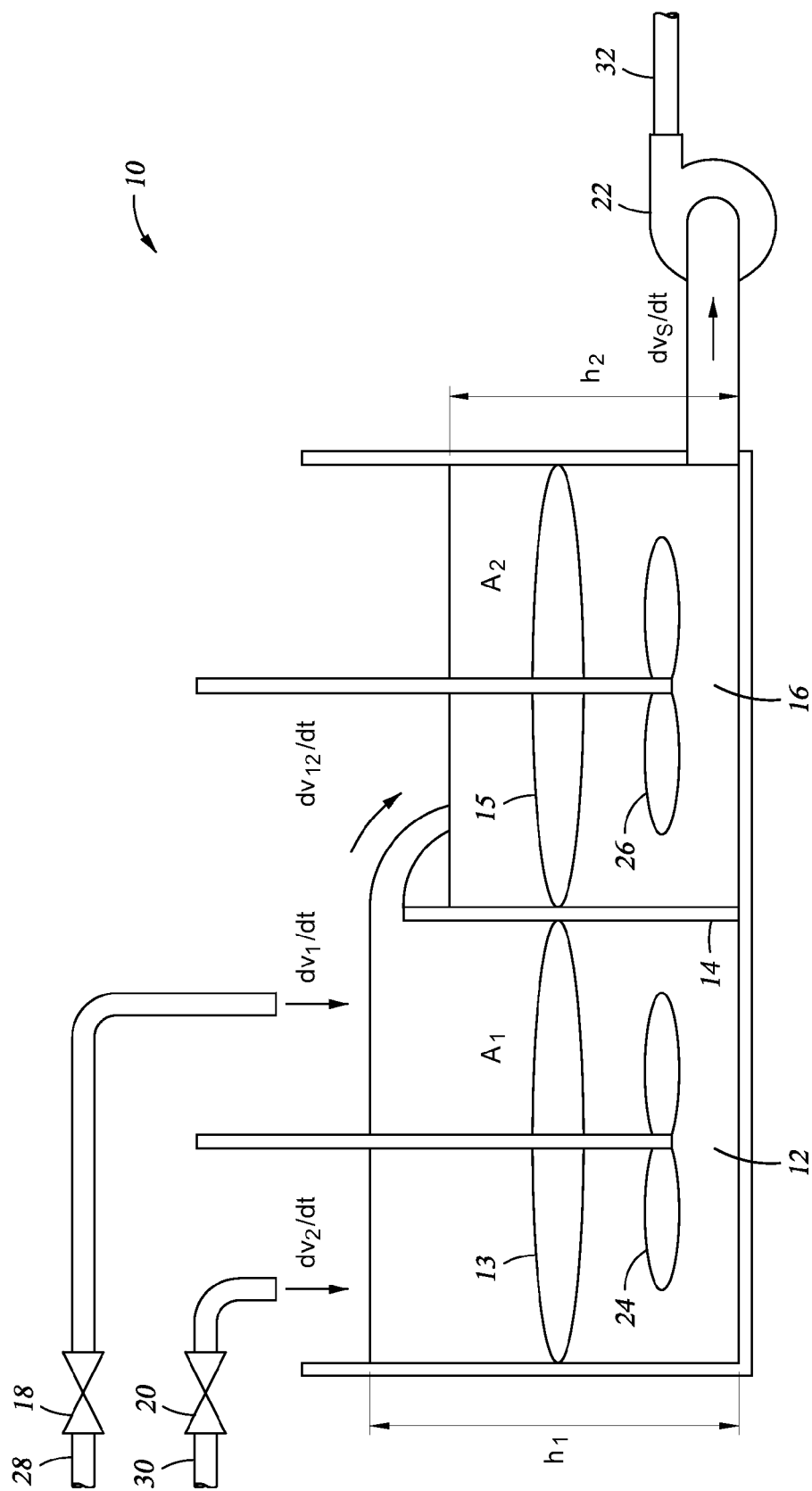
FIG. 1 is a diagram of one embodiment of a physical plant within which a control system for a mixing system may be implemented.

In an embodiment shown in FIG. 1, a physical plant 10 to be controlled comprises a first tank 12 joined by a weir 14 to a second tank 16, a first actuator 18 dispensing a first material to be mixed, a second actuator 20 dispensing a second material to be mixed, and an outflow pump 22. A first mixture 13 is formed from the in-flow of the first material from the first actuator 18 and the second material from the second actuator 20 into the first tank 12. When the first mixture 13 fills the first tank 12 to the height of the weir 14, the first mixture 13 overflows into the second tank 16. The mixture in the second tank 16 is referred to as a second mixture 15. A first stirrer 24 and a second stirrer 26 may be provided to promote homogeneity of the first mixture 13 in the first tank 12 and the second mixture 15 in the second tank 16, respectively. The second mixture 15 exits the second tank 16 via an outflow pump 22 and a discharge line 32. In other embodiments, additional actuators may feed additional materials into the first tank 12. In other embodiments, a single tank or three or more tanks may be used.

In an embodiment, the physical plant 10 is a well bore servicing fluid mixing system, such as, for example, a cement mixer used to provide a continuous stream of a cement slurry for cementing a tubular casing against a well bore wall. In this embodiment, a dry cement material may be fluidized by the introduction of pressurized air, which promotes fluid flow of the dry cement through a first feed line 28, to be dispensed into the first tank 12 through the first actuator 18, for example, and a carrier fluid, such as water, for example, may flow through a second feed line 30 to be dispensed into the first tank 12 through the second actuator 20. In this embodiment, the first and second actuators 18, 20 may be valves, for example. These two materials, the dry cement material and the carrier fluid, are mixed by the first stirrer 24 to obtain the first mixture 13. Non-fluidized sand or other particulate matter may be dispensed through a third actuator (not shown), such as a screw feeder, for example, into the first tank 12 to mix with the cement slurry. In various embodiments, any of the actuators may comprise a valve, a screw feeder, an augur, an elevator, or other type of actuator known to those skilled in the art. The first mixture 13 is preferably substantially homogenous. The physical plant 10 should provide the cement slurry via the outflow pump 22 and the discharge line 32 at a volumetric flow rate sufficient to support the well bore servicing operation, and should mix the dry concrete material, the carrier fluid, and any particulate material in appropriate proportions so that the cement slurry dispensed thereby achieves a desired density. The physical plant 10 in other embodiments may support other mixing operations of other materials. For example, in another embodiment, proppants and a carrier fluid may be dispensed through the first and second actuators 18, 20 into the first tank 10 to form a portion of a fracturing fluid.

Figure 2:
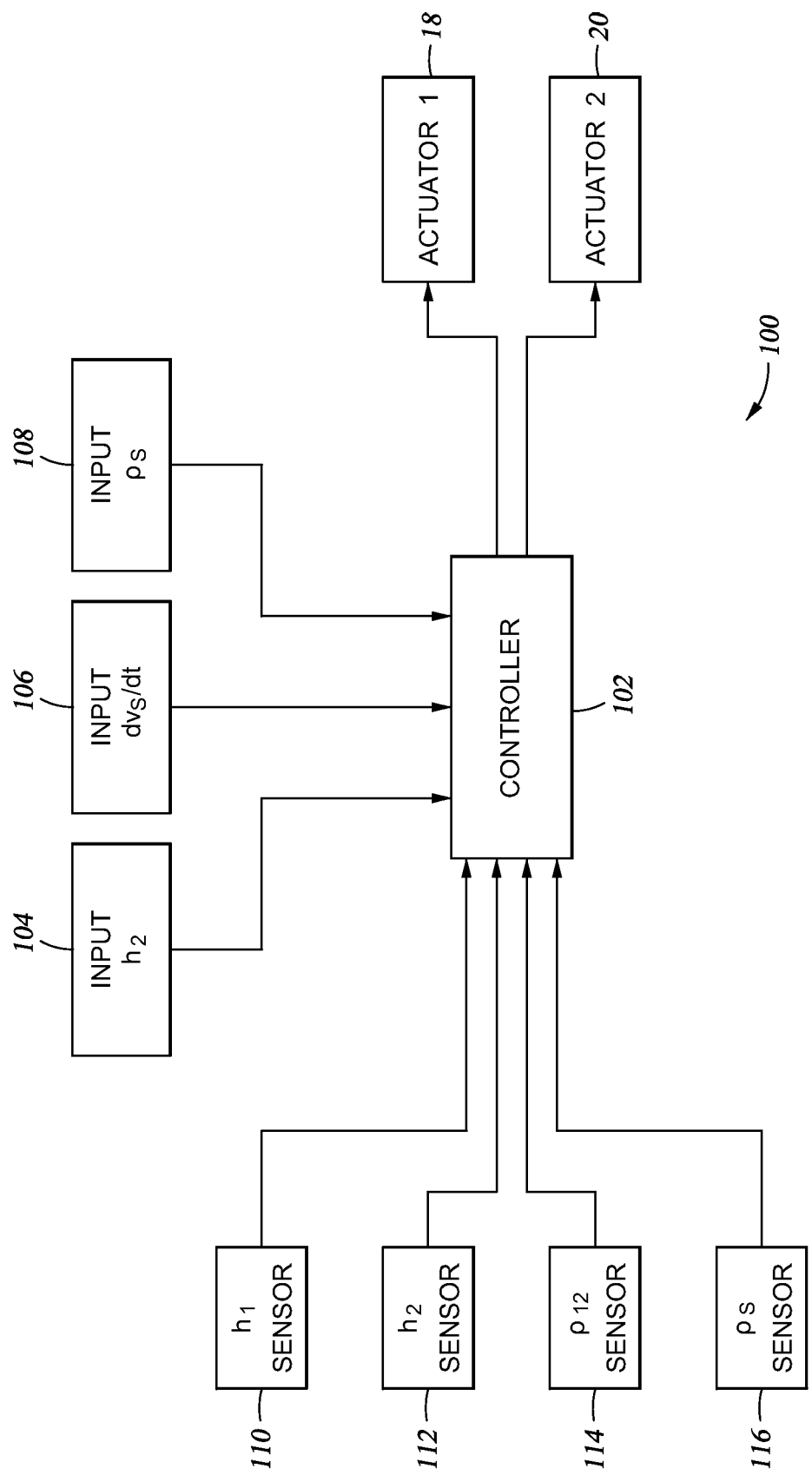
FIG. 2 is a block diagram of one embodiment of a control system.

FIG. 1 also identifies several parameters of a control system, e.g., a first control system 100 depicted in FIG. 2, coupled to the physical plant 10 and functional to control the operation thereof. The first tank 12 has a cross-sectional area represented by the constant $A_1$, and the second tank 16 has a cross-sectional area represented by the constant $A_2$. The height of the first mixture 13 in the first tank 12 is represented by the variable $h_1$, and the height of the second mixture 15 in the second tank 16 is represented by the variable $h_2$. The volumetric flow rate of the first material, for example dry cement, through the first actuator 18 into the first tank 12 is represented by $dv_1/dt$. The volumetric flow rate of the second material, for example water, through the second actuator 20 into the first tank 12 is represented by $dv_2/dt$. The volumetric flow rate of the first mixture 13, for example a cement slurry, over the weir 14 into the second tank 16 is represented by $dv_{12}/dt$. The volumetric flow rate of the second mixture 15 out of the second tank 16 and through the outflow pump 22 is represented by $dv_s/dt$.

The first control system 100 disclosed hereinafter is expected to reduce control oscillations due to system time lags and to promote independent control of a mixture density and a mixture flow rate.

Turning now to FIG. 2, a first control system 100 is depicted that is coupled to the physical plant 10 of FIG. 1 and controls the first actuator 18 and the second actuator 20. In an embodiment, the first control system 100 controls the actuators 18, 20 to obtain sensed parameter values that approach or equal the following input parameter values that are input into the first control system 100 by an operator through an interface with the first control system 100: a height $h_2$ of the second mixture 15 in the second tank 16, a volumetric flow rate $dv_s/dt$ of the second mixture 15 out of the second tank 16, and a density $\rho_s$ of the second mixture 15 out of the second tank 16. In other embodiments, the first control system 100 may control the first actuator 18 and the second actuator 20 to obtain sensed parameter values that approach or equal other input parameter values. For example, the first control system 100 may be said to control the volumetric flow rate of the first mixture 13 over the weir 14 into the second tank 16, represented by $dv_{12}/dt$, and the density of the second mixture 15 as it leaves the second tank 16, represented by $\rho_s$. However, the first control system 100 actually controls the first actuator 18 and the second actuator 20, for example, by adjusting a valve position or by modifying a rotation rate of a screw feeder.

The first control system 100 comprises a controller 102 that receives input parameter values from an operator through an interface with the first control system 100, and also receives sensed parameter values from sensors coupled to or integral with the physical plant 10. The controller 102 distributes as output parameter values commands to the first actuator 18 and the second actuator 20. An input parameter value 104 for $h_2$ provides to the controller 102 the desired height $h_2$ of the second mixture 15 in the second tank 16, an input parameter value 106 for $dv_s/dt$ provides the desired volumetric flow rate $dv_s/dt$ of the second mixture 15 out of the second tank 16, and an input parameter value 108 for $\rho_s$ provides the desired density $\rho_s$ of the second mixture 15 out of the second tank 16. A $h_1$ sensor 110 provides an indication of the height $h_1$ of the first mixture 13 in the first tank 12, a $h_2$ sensor 112 provides an indication of the height $h_2$ of the second mixture 15 in the second tank 16, a $\rho_{12}$ sensor 114 provides an indication of the density $\rho_{12}$ of the first mixture 13, and a $\rho_s$ sensor 116 provides an indication of the density $\rho_s$ of the second mixture 15. These indications may be referred to as sensed parameter values.

In an embodiment, the first control system 100 controls the actuators 18, 20 to achieve a desired volumetric flow rate $dv_{12}/dt$ of the first mixture 13 over the weir 14 into the second tank 16, and a density $\rho_s$ of the second mixture 15 out of the second tank 16, independently of each other. For example, changing the $dv_s/dt$ input parameter value 106 causes the controller 102 to control the actuators 18, 20 so that the actual volumetric flow rate $dv_{12}/dt$ of the first mixture 13 over the weir 14 into the second tank 16 changes until it substantially equals the $dv_s/dt$ input parameter value 106. Actual values may also be referred to as nominal values in some contexts by those skilled in the control systems art. However, the density $\rho_s$ of the second mixture 15 as it leaves the second tank 16 remains substantially unchanged because the density and flow rate parameters are controlled independently. Similarly, changing the $\rho_s$ input parameter value 108 causes the controller 102 to alter the control signals to actuators 18, 20 until the sensed density $\rho_s$ of the second mixture 15 as read by the $\rho_s$ sensor 116 substantially equals the $\rho_s$ input parameter value 108. However, the volumetric flow rate $dv_{12}/dt$ of the first mixture 13 over the weir 14 into the second tank 16 remains substantially unchanged because the flow rate and density parameters are controlled independently.

Figure 3:
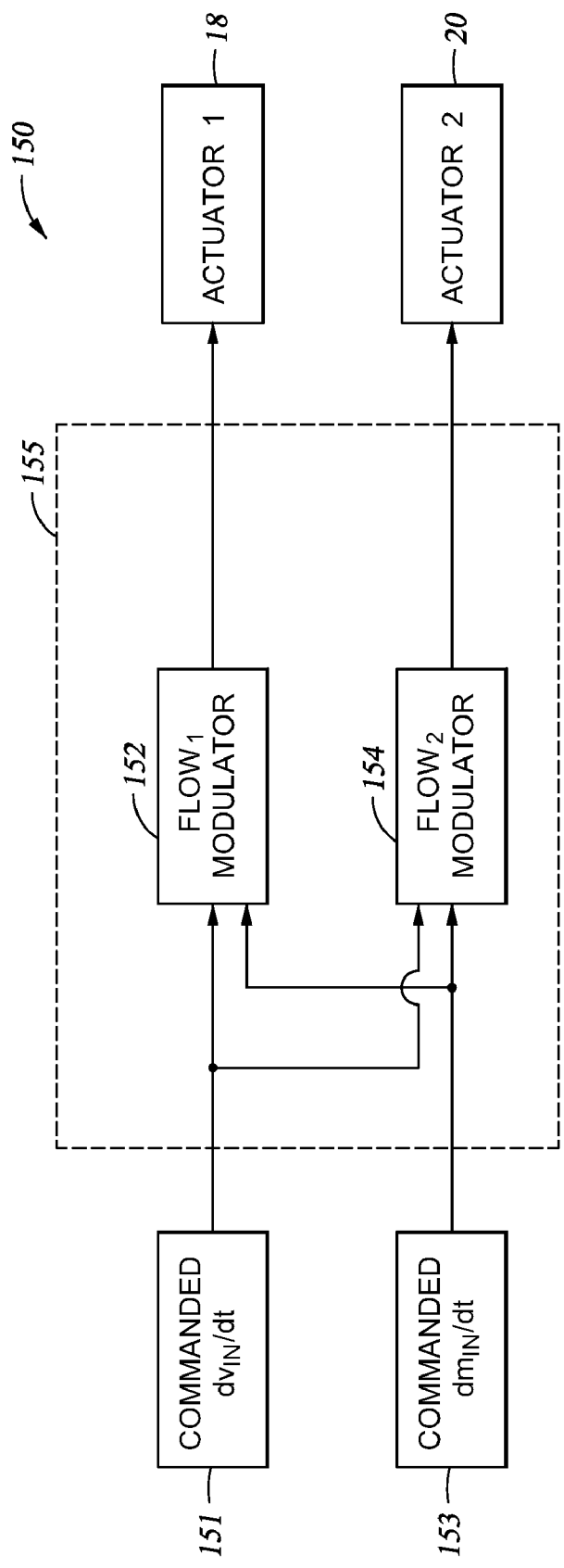
FIG. 3 is a block diagram of one embodiment of a flow modulator component of the control system of FIG. 2.

Turning now to FIG. 3, a flow modulator 150 for use with one or more embodiments of the first control system 100 is depicted. The flow modulator 150 comprises a first flow modulator 152 and a second flow modulator 154 to modulate the first actuator 18 and the second actuator 20, respectively. In some embodiments, the first flow modulator 152 and the second flow modulator 154 may be combined in an integrated modulator unit 155 or combined in a single functional block, such as, for example, within a computer programmed to modulate the first actuator 18 and the second actuator 20. The first and second flow modulator 152, 154 provide a mechanism for modulating or converting between the preferred control parameters, for example volumetric rate and mass flow rate, and the physical controls of the physical system, for example control signals to the first actuator 18 and the second actuator 20. Both the first flow modulator 152 and the second flow modulator 154 receive from another component of the controller 102 a commanded first volume flow rate signal 151 for $dv_{in}/dt$ and a commanded first mass flow rate signal 153 for $dm_{in}/dt$. For example, the commanded first volume flow rate $dv_{in}/dt$ signal 151 and the commanded first mass flow rate $dm_{in}/dt$ signal 153 may be received from a flow regulator 200 to be discussed hereinafter, or from some other component of the controller 102. The commanded first volume flow rate $dv_{in}/dt$ signal 151 corresponds to a desired combined volumetric in-flow rate of materials, for example dry cement and carrier fluid, from the first actuator 18 and the second actuator 20 into the first tank 12. The commanded first mass flow rate $dm_{in}/dt$ signal 153 represents a desired combined mass in-flow rate of these materials from the first actuator 18 and the second actuator 20 into the first tank 12.

In an embodiment, the flow modulator 150 generates an actuator$_1$ signal to control the first actuator 18, and this actuator$_1$ signal may be expressed mathematically as proportional to a function $f_1$ as follows:

$$\text{actuator}_1 \text{ signal} \propto f_1 = [dm_{in}/dt - (dv_{in}/dt)\rho_{m2}]/(\rho_1 - \rho_{m2}) \quad (1)$$

Similarly, the flow modulator 150 generates an actuator$_2$ signal to control the second actuator 20, and the actuator$_2$ signal may be expressed mathematically as proportional to a function $f_2$ as follows:

$$\text{actuator}_2 \text{ signal} \propto f_2 = [(dv_{in}/dt)\rho_{m1} - dm_{in}/dt]/(\rho_{m1} - \rho_{m2}) \quad (2)$$

where $dm_{in}/dt$ is the combined mass flow rate entering the tank, $dv_{in}/dt$ is the combined volume flow rate entering the tank, $\rho_{m1}$ is the density of the first material, for example dry cement, flowing into the first tank 12 from the first actuator 18, and where $\rho_{m2}$ is the density of the second material, for example water, flowing into the first tank 12 from the second actuator 20. One skilled in the art will readily be able to determine a suitable first constant of proportionality for equation (1) to drive the first actuator 18 and a suitable second constant of proportionality for equation (2) to drive the second actuator 20 in a particular embodiment. In an embodiment, the actuator$_1$ and actuator$_2$ signals may be conditioned by one or more components (not shown) between the flow modulator 150 and the actuators 18, 20 to conform the actuator$_1$ and actuator$_2$ signals to a non-linear response of one or more of the actuators 18, 20.

Figure 4:
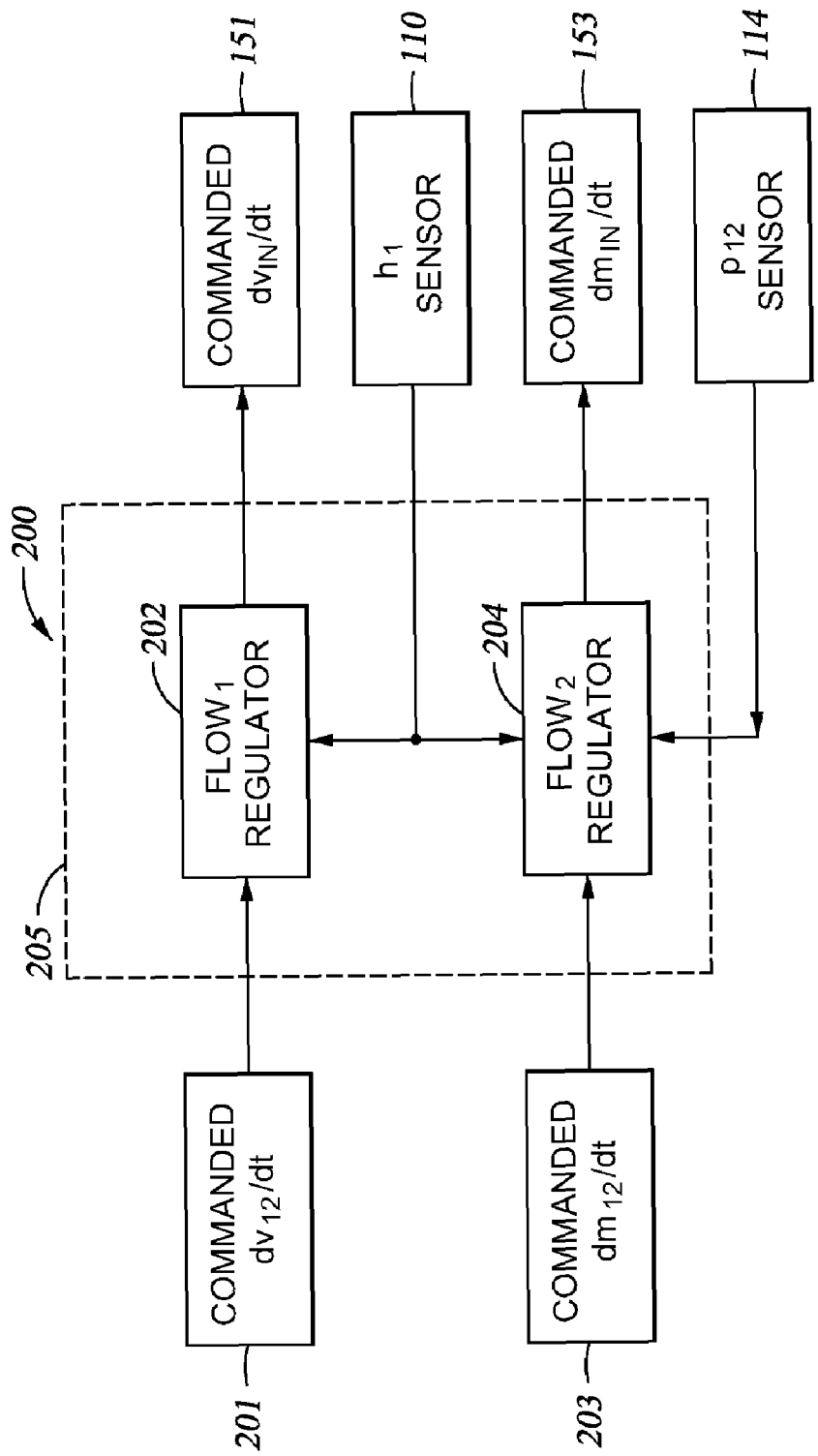
FIG. 4 is a block diagram of one embodiment of a flow regulator component of the control system of FIG. 2.

Turning now to FIG. 4, a flow regulator 200 for use with one or more embodiments of the first control system 100 is depicted. The flow regulator 200 comprises a first flow regulator 202 and a second flow regulator 204. In some embodiments, the first flow regulator 202 and the second flow regulator 204 may be combined in an integrated unit 205 or combined in a single functional block, such as, for example, within a computer programmed to perform flow regulation. The first flow regulator 202 receives from another component of the controller 102 a commanded volumetric flow rate signal 201 for $dv_{12}/dt$ of the first mixture 13 over the weir 14 into the second tank 16, and a sensed height $h_1$ of the first mixture 13 in the first tank 12 from the $h_1$ sensor 110. The first flow regulator 202 may receive the commanded volumetric flow rate $dv_{12}/dt$ signal 201, for example, from a flow$_1$ state feedback controller with command feed forward 250, to be discussed hereinafter, or from some other component of the controller 102. The first flow regulator 202 generates the commanded first volumetric flow rate $dv_{in}/dt$ signal 151 that is received as a commanded value by the flow modulator 150 or by the first and second flow modulators 152, 154 as described above with reference to FIG. 3.

The second flow regulator 204 receives from another component of the controller 102 a commanded mass flow rate signal 203 for $dm_{12}/dt$ of the first mixture 13 over the weir 14 into the second tank 16, a sensed height $h_1$ of the first mixture 13 in the first tank 12 from the $h_1$ sensor 110, and a sensed density $\rho_{12}$ of the first mixture 13 from sensor 114. The second flow regulator 202 may receive the commanded mass flow rate $dm_{12}/dt$ signal 203, for example, from a flow$_2$ state feedback controller with command feed forward 252, to be discussed hereinafter, or from some other component of the controller 102. The second flow regulator 204 generates the commanded first mass flow rate $dm_{in}/dt$ signal 153 that is received as a commanded value by the flow modulator 150 or by the first and second flow modulators 152, 154 described above with reference to FIG. 3.

In an embodiment, the function of the first flow regulator 202 may be expressed mathematically as:

$$\text{commanded } dv_{in}/dt = F(h_1)(1-K_v) + K_v(\text{commanded } dv_{12}/dt) \quad (3)$$

and the function of the second flow regulator 204 may be expressed mathematically as:

$$\text{commanded } dm_{in}/dt = F(h_1)\rho_{12}(1-K_m) + K_m(\text{commanded } dm_{12}/dt) \quad (4)$$

where $F(h_1)$ is a non-linear function of the height $h_1$ of the first mixture 13 in the first tank 12 and provides an estimate of a volumetric flow rate $dv_{12}/dt$ of the first mixture 13 over the weir 14 into the second tank 16; where commanded $dv_{12}/dt$ is the commanded volumetric flow rate $dv_{12}/dt$ signal 201; where commanded $dm_{12}/dt$ is the commanded mass flow rate $dm_{12}/dt$ signal 203; where $\rho_{12}$ is an indication of density of the first mixture 13 in the first tank 12 based on the input from the $\rho_{12}$ sensor 114; and where $K_v$ and $K_m$ are constants of proportionality that are greater than zero. The values for $K_v$ and $K_m$ may be chosen through a closed form solution and/or iteratively so as to minimize overall response time while maintaining stability and desired flow rate and density trajectories during transition phases. An exemplary non-linear function $F(h_1)$ for volumetric flow rate over a rectangular weir is given in *Engineering Fluid Mechanics,* 5th Edition, by Roberson and Crowe, published by Houghton Mifflin, 1993, and may be represented as:

$$dv_{12}/dt=F(h_1)=KL(h_1-h_w)^{(3/2)} \qquad (5)$$

where L is the length of the weir 14 dividing the tanks 12, 16, K is a flow coefficient that may be empirically determined over a set of operating conditions for a specific weir geometry, and $h_w$ is a constant representing the height of the weir.

The volumetric outflow of the first mixture 13 $dv_{12}/dt$ and the mass outflow of the first mixture 13 $dm_{12}/dt$ from the first tank 12 to the second tank 16 may be modeled as negative state feedbacks in the physical plant 10. In equation (3), the effect of the $1\times F(h_1)$ term is to cancel or decouple the negative state feedback associated with $dv_{12}/dt$, and in equation (4), the effect of the $1\times\rho_{12}F(h_1)$ term is to decouple the negative state feedback associated with $dm_{12}/dt$. The control system 102 may be more robust as a result of the state feedback decoupling in the first and second flow regulators 202, 204 because the control system 102 only has to correct for errors between desired and actual mass rate and desired and actual volumetric flow rate without having to also compensate for the first mixture 13 leaving the first tank 12.

Figure 5A:
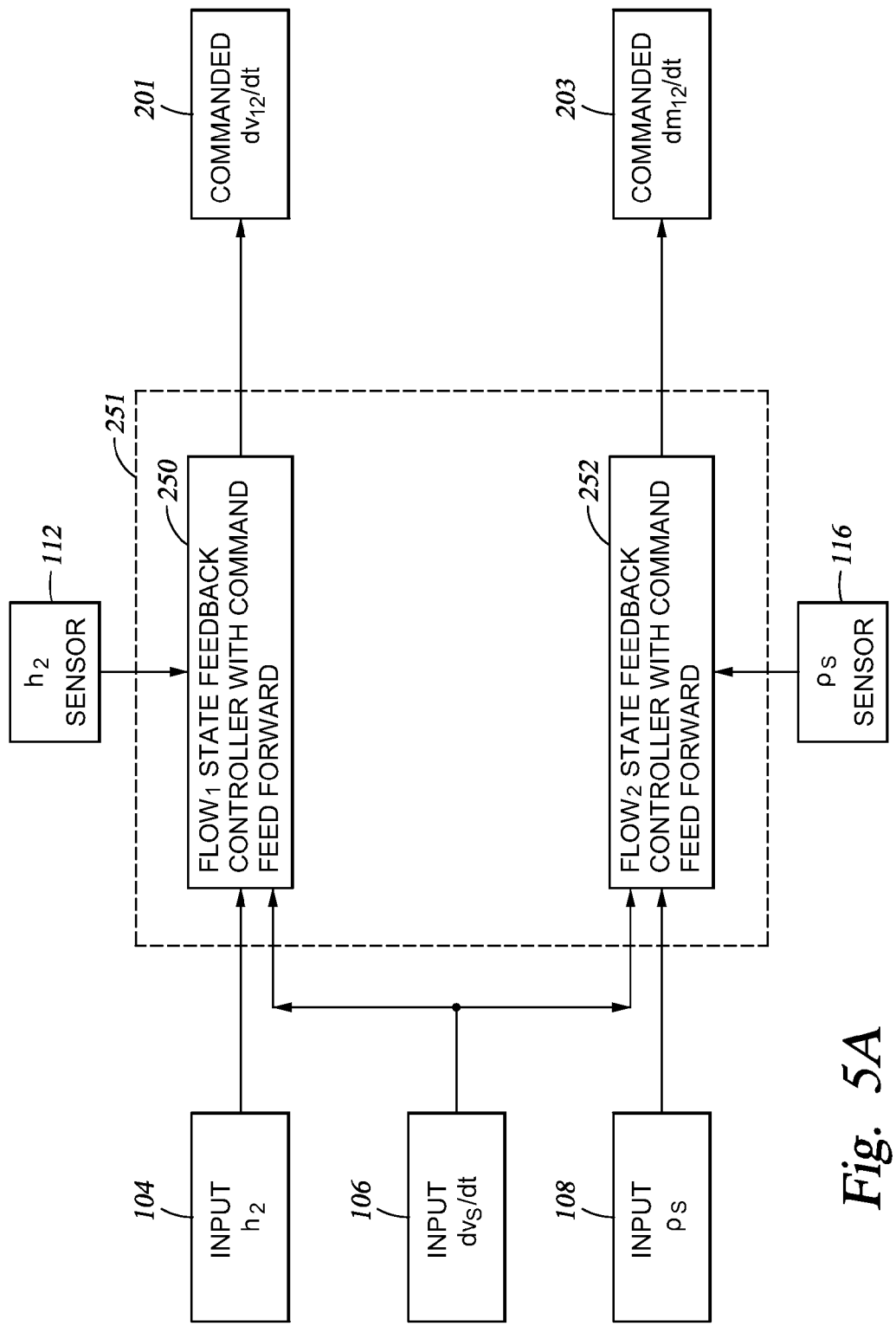
FIG. 5A is a block diagram of two embodiments of a state feedback controller with command feed forward component of the control system of FIG. 2.

Turning now to FIG. 5A, a flow$_1$ state feedback controller with command feed forward 250 and a flow$_2$ state feedback controller with command feed forward 252 for use with one or more embodiments of the first control system 100 are depicted. The flow$_1$ state feedback controller with command feed forward 250 receives the $h_2$ input parameter value 104 and the $dv_s/dt$ input parameter value 106 from an operator interfacing with the first control system 100, and also receives an indication of the height $h_2$ of the second mixture 15 in the second tank 16 from the $h_2$ sensor 112. Based on these inputs, the flow$_1$ state feedback controller with command feed forward 250 produces the commanded volumetric flow rate $dv_{12}/dt$ signal 201 that is received as a commanded value by the first flow regulator 202 described above with reference to FIG. 4. The flow$_1$ state feedback controller with command feed forward 250 may also be referred to as a height controller with command feed forward.

The flow$_2$ state feedback controller with command feed forward 252 receives the $dv_s/dt$ input parameter value 106 and the $\rho_s$ input parameter value 108, from an operator interfacing with the first control system 100, and also receives an indication of the density $\rho_s$ of the second mixture 15 in the second tank 16 from the $\rho_s$ sensor 116. Based on these inputs, the flow$_2$ state feedback controller with command feed forward 252 produces the commanded mass flow rate $dm_{12}/dt$ signal 203 that is received as a commanded value by the second flow regulator 204 described above with reference to FIG. 4. The flow$_2$ state feedback controller with command feed forward 252 may also be referred to as a density controller with command feed forward. The flow state feedback controllers with command feed forward 250, 252 receive different inputs but serve the same purpose of providing a commanded value signal to a flow regulator 202, 204. In some embodiments, the flow$_1$ state feedback controller with command feed forward 250 and the flow$_2$ state feedback controller with command feed forward 252 may be combined in an integrated unit 251 or combined in a single functional block, such as, for example, within a computer programmed to perform the indicated functions.

Figure 5B:
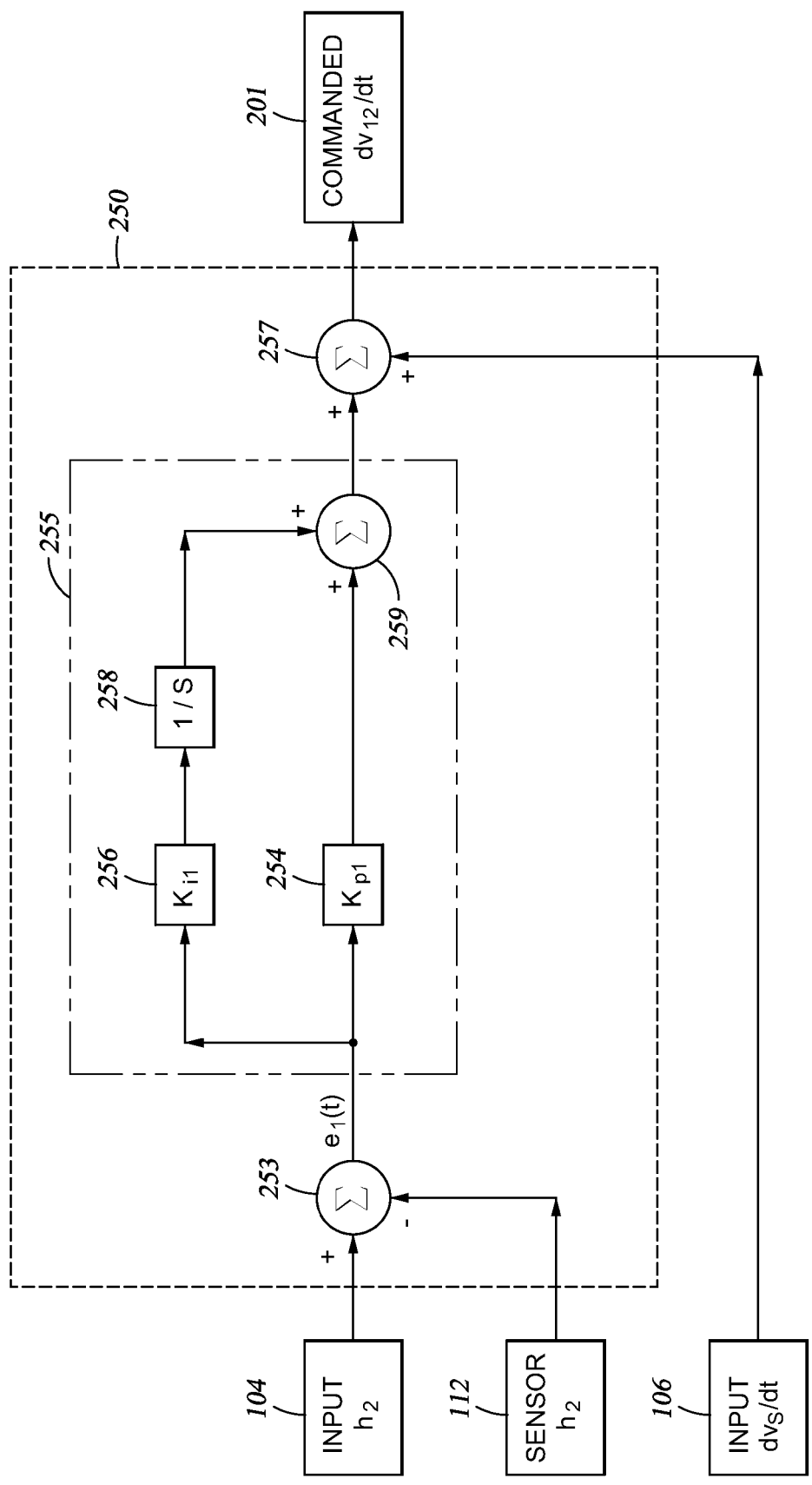
FIG. 5B is a block diagram of the first embodiment of the state feedback controller with command feed forward component of FIG. 5A.

Turning now to FIG. 5B, a block diagram shows processing details of one embodiment of the flow$_1$ state feedback controller with command feed forward 250. A first summation component 253, represented by the $\Sigma$ symbol within a circle as is conventional in mathematical notation, determines a first error term $e_1(t)$ by negatively summing the indication of the height $h_2$ of the second mixture 15 in the second tank 16 from the $h_2$ sensor 112 with the $h_2$ input parameter value 104. The inputs to any summation component, for example the first summation component 253, are positively or negatively summed together to determine the output of the summation component. Specifically, the inputs associated with a "+" (plus) sign are positively summed, while the inputs associated with a "−" (minus) sign are negatively summed. The output of the first summation component 253, namely the first error term $e_1(t)$, is then processed by a first proportional-integral (PI) controller 255 having a gain $K_{p1}$ for a first proportional component 254 and an integral gain $K_{i1}$ for a first integral component 256 associated with a first integration factor 258, as represented by 1/S inside the box, as is conventional in control system art to suggest integration. The proportional and integral operations on the first error term $e_1(t)$ are positively summed by a second summation component 259. A twenty-fifth summation component 257 sums the output of the second summation component 259 with the $dv_s/dt$ input parameter value 106 of the second mixture 15 out of the second tank 16. The output of the twenty-fifth summation component 257 is the commanded volumetric flow rate $dv_{12}/dt$ signal 201 that is received as a commanded value by the first flow regulator 202 described above with reference to FIG. 4. The temporal response of the flow$_1$ state feedback controller with command feed forward 250, represented as a function $u_1(t)$, may be expressed mathematically as:

$$\text{commanded } dv_{12}/dt=u_1(t)=dv_s/dt+K_{p1}e_1(t)+K_{i1}\int e_1(t)dt \qquad (6)$$

The outflow of the second mixture 15 from the second tank 16 may be modeled as negative state feedback in the physical plant 10. In equation (6), the effect of the $dv_s/dt$ term, which is the command feed forward term, is to decouple the negative state feedback associated with the outflow of the second mixture 15 from the second tank 16. While this may not be strict state feedback decoupling, the same benefits of robustness may be at least partially obtained using this technique.

Figure 5C:
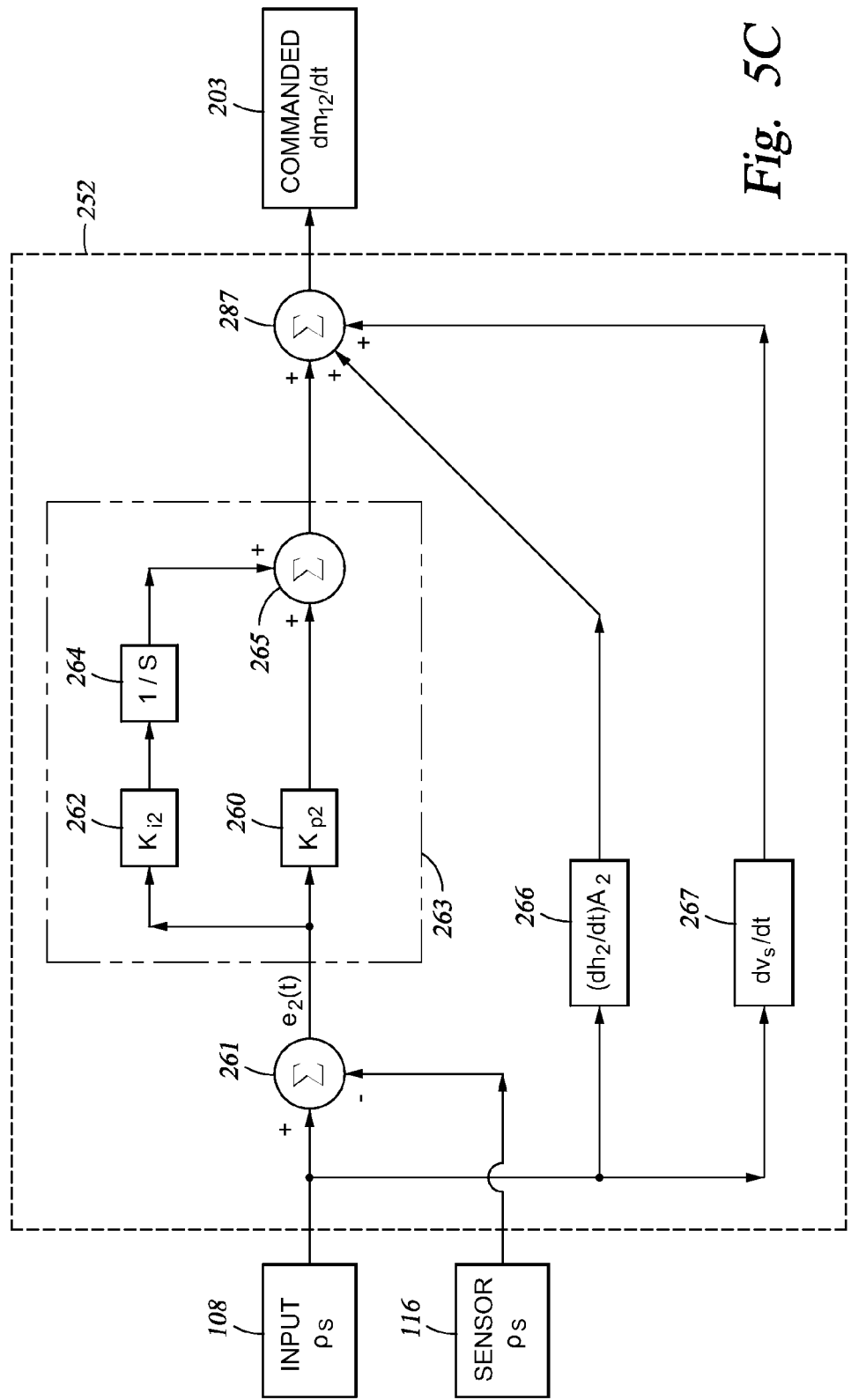
FIG. 5C is a block diagram of the second embodiment of the state feedback controller with command feed forward component of FIG. 5A.

Turning now to FIG. 5C, a block diagram shows processing details of one embodiment of the flow$_2$ state feedback controller with command feed forward 252. A third summation component 261 determines a second error term $e_2(t)$ by negatively summing the indication of the density $\rho_s$ of the second mixture 15 in the second tank 16 from the $\rho_s$ sensor 116 with the $\rho_s$ input parameter value 108. The second error term $e_2(t)$ is then processed by a second PI controller 263 having a gain $K_{p2}$ for a second proportional component 260 and an integral gain $K_{i2}$ for a second integral component 262 associated with a second integration factor 264. The proportional and integral operations on the second error term $e_2(t)$ are positively summed by a fourth summation component 265. A twenty-sixth summation component 287 sums the output of the fourth summation component 265 with the output of a first multiplier component 266 and the output of a second multiplier component 267. The first multiplier component 266 output equals the $\rho_s$ input parameter value 108 multiplied by $(dh_2/dt)A_2$, where $A_2$ is the cross-sectional area of the second tank 16 and $dh_2/dt$ is the height rate of change of the second mixture 15 in the second tank 16. In an embodiment, the first multiplier component 266 may be omitted, as for example when the parameter $dh_2/dt$ is not readily available. The second multiplier component 267 outputs the product of the $\rho_s$ input parameter value 108 multiplied by the input parameter value 106 of $dv_s/dt$ of the second mixture 15 out of the second tank 16. The output of the twenty-sixth summation component 287 is the commanded mass flow rate $dm_{12}/dt$ signal 203 that is received as a commanded value by the second flow regulator 204 described above with reference to FIG. 4. Thus, the temporal response of the $flow_2$ state feedback controller with command feed forward 252, represented as a function $u_2(t)$, may be expressed mathematically as:

$$\text{commanded } dm_{12}/dt = u_2(t) = \text{input}\rho_s\{(dh_2/dt)A_2 + dv_s/dt\} + K_{p2}e_2(t) + K_{i2}\int e_2(t)dt \quad (7)$$

The outflow of mass from the second tank 16 may be modeled as negative state feedback in the physical plant 10. In equation (7), the effect of the $\rho_s(dv_s/dt)$ term, the command feed forward term, is to decouple the negative state feedback associated with the outflow of mass from the second tank 16. While this may not be strict state feedback decoupling, the same benefits of robustness may be at least partially obtained using this technique. An additional refinement of this relaxed state feedback decoupling technique may be obtained by decoupling the effect of a loss of mass associated with changes of height of the second mixture 15 in the second tank 16. In equation (7), the $\rho_s(dh_2/dt)A_2$ term also contributes to decoupling the negative state feedback associated with the outflow of mass from the second tank 16. The $dh_2/dt$ factor may be determined from a series of indications of the height of the second mixture 15 in the second tank 16 or by other means such as an estimate of $dh_2/dt$ produced by a height observer as discussed below.

One skilled in the art will recognize that the results of the analysis of the $flow_1$ state feedback controller with command feed forward 250 and the $flow_2$ state feedback controller with command feed forward 252 above may be applied to digital signals as well as analog signals. For example, analog parameters such as the indication of density $\rho_s$ of the second mixture 15 in the second tank 16 from the $\rho_s$ sensor 116 may be converted by an analog-to-digital converter (D/A converter) to a digital signal. Similarly, analog outputs may be produced by a digital-to-analog converter (A/D converter), optionally combined with an amplifier to provide sufficient power to drive an electromechanical device, converting a digital control signal to an analog control signal suitable for controlling the first actuator 18 and the second actuator 20.

Figure 6:
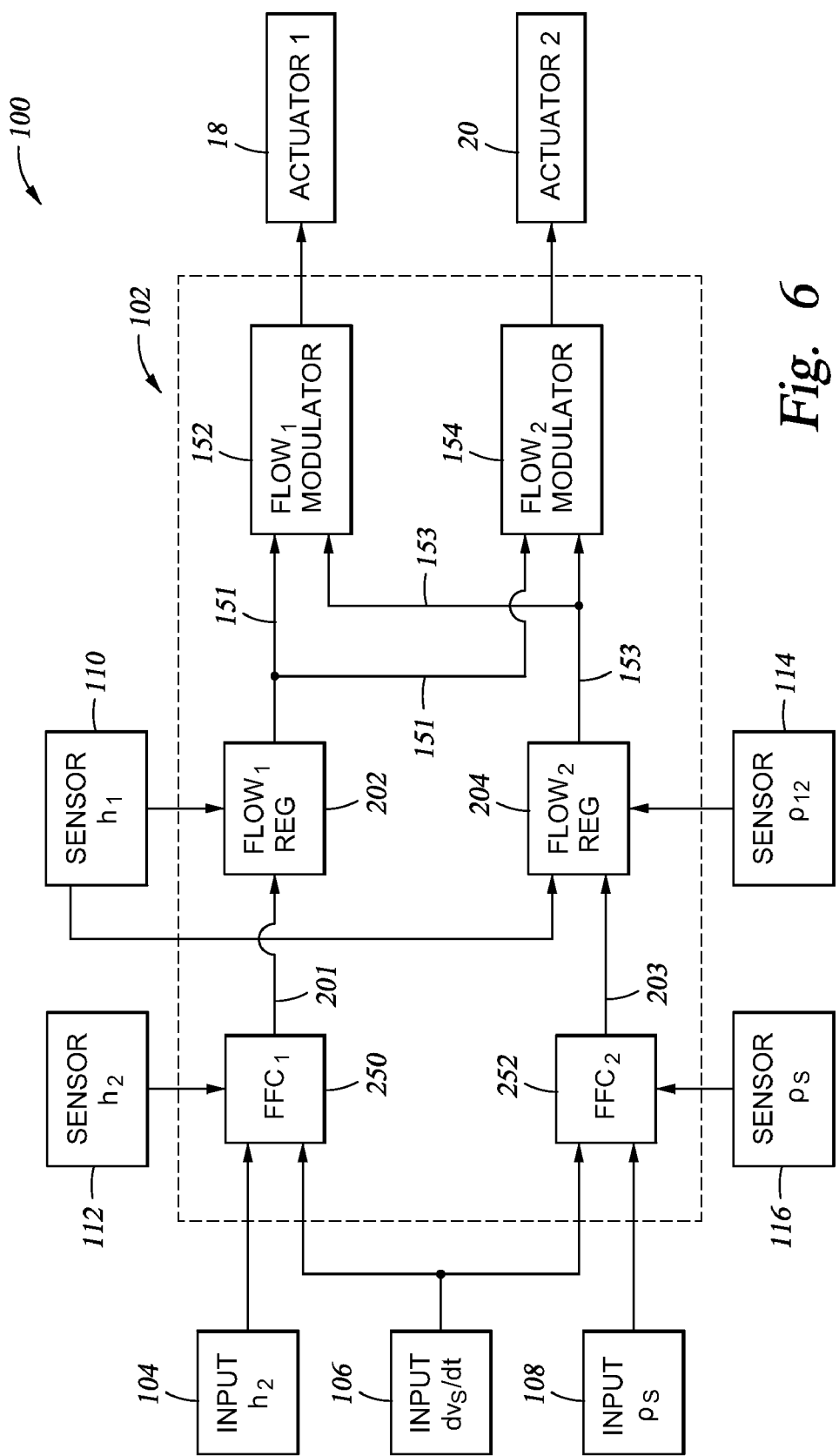
FIG. 6 is a block diagram of the components of the control system of FIG. 2 in the context of the physical plant.

Turning now to FIG. 6, the major components of the first control system 100 are depicted coupled together and to the actuators 18, 20 of the physical plant 10 described above with reference to FIG. 1. In particular, FIG. 6 depicts an embodiment of the first control system 100 of FIG. 2, showing the various components that may comprise the controller 102.

Referring to the right side of the drawing, the first and second flow modulators 152, 154, as described above with reference to FIG. 3, are shown cross-coupled and connected to control the first and second actuators 18, 20. The first flow modulator 152 receives the commanded first volume flow rate $dv_{in}/dt$ signal 151 from the first flow regulator 202 and the commanded first mass flow rate $dm_{in}/dt$ signal 153 from the second flow regulator 204 to generate an $actuator_1$ control signal to control the first actuator 18. The second flow modulator 154 receives the commanded first volume flow rate $dv_{in}/dt$ 151 signal from the first flow regulator 202 and the commanded first mass flow rate $dm_{in}/dt$ 153 signal from the second flow regulator 204 to generate an $actuator_2$ control signal to control the second actuator 20. Thus, the first and second flow modulators 152, 154 may be said to control the actuators 18, 20 based on the $dv_{in}/dt$ and $dm_{in}/dt$ system parameters, which are not the parameters desired to be controlled. Instead, these system parameters $dv_{in}/dt$ and $dm_{in}/dt$ are associated closely with the operation of the first and second actuators 18, 20 by the flow modulators 152, 154. However, it is desired to control other system parameters, namely the input parameter values, which are derived from the states of the first and second actuators 18, 20 and the characteristics of the physical plant 10, for example the cross-sectional area of the first and second tanks 12, 16, and are time lagged with respect to the states of the actuators 18, 20. The possible states of the actuators 18, 20 depend on the actuator type. For example, a valve opens or closes, whereas a screw feeder turns at different speeds. The various other components of the controller 102, which will be discussed herein, enable control of the desired system parameters by bridging between the states of the actuators 18, 20 and those parameters desired to be controlled.

The first flow regulator 202 receives the commanded volumetric flow rate $dv_{12}/dt$ signal 201 from the $flow_1$ state feedback controller with command feed forward 250 and the $h_1$ indication from the $h_1$ sensor 110 to generate the commanded first volume flow rate $dv_{in}/dt$ signal 151 that feeds into the flow modulators 152, 154. As discussed above with reference to FIG. 4, the first flow regulator 202 uses the indication of $h_1$ to decouple the negative state feedback associated with the flow of the first mixture 13 out of the first tank 12. For example, the volumetric outflow can be determined from $F(h_1)$, as discussed above, and then the volumetric outflow can be decoupled.

The second flow regulator 204 receives the commanded mass flow rate $dm_{12}/dt$ signal 203 from the $flow_2$ state feedback controller with command feed forward 252, the indication from the $h_1$ sensor 110, and the $\rho_{12}$ indication from the $\rho_{12}$ sensor 114 to generate the commanded first mass flow rate $dm_{in}/dt$ signal 153 that feeds into the flow modulators 152, 154. As discussed above with reference to FIG. 4, the second flow regulator 204 uses the indications of $h_1$ and of $\rho_{12}$ to decouple the negative state feedback associated with the flow of the first mixture 13 out of the first tank 12. For example, the mass outflow can be calculated from the product of the indication of $\rho_{12}$ and the volumetric outflow $dv_{12}/dt$, where the volumetric outflow $dv_{12}/dt$ is determined from $F(h_1)$, and the mass outflow then can be decoupled. The first and second flow regulators 202, 204 may be said to provide one level of removal from the system parameters $dv_{in}/dt$ and $dm_{in}/dt$ directly associated with the states of the first and second actuators 18, 20.

The $flow_1$ state feedback controller with command feed forward 250 receives the $h_2$ input parameter value 104 and the $dv_s/dt$ input parameter value 106 from an operator interfacing with the first control system 100, and also receives the indication of $h_2$ from the $h_2$ sensor 112 to generate the commanded volumetric flow rate $dv_{12}/dt$ signal 201 that feeds into the first flow regulator 202. As discussed above, the $flow_1$ state feedback controller with command feed forward 250 may be referred to as a height controller, because it controls the height $h_2$ of the second mixture 15 in the second tank 16. The command feed forward term, namely the $dv_s/dt$ input parameter value 106, may be considered to decouple the negative state feedback of volumetric flow out of the second tank 16 as discussed above with reference to FIG. 5B.

The flow$_2$ state feedback controller with command feed forward 252 receives the $dv_s/dt$ input parameter value 106 and the $\rho_s$ input parameter value 108 from an operator interfacing with the first control system 100, and also receives the indication of $\rho_s$ from the $\rho_s$ sensor 116 to generate the commanded mass flow rate $dm_{12}/dt$ signal 203 that feeds into the second flow regulator 204. As discussed above, the flow$_2$ state feedback controller with command feed forward 252 may be referred to as a density controller, because it controls the density $\rho_s$ of the second mixture 15 in the second tank 16. The command feed forward term, formed by the product of the $\rho_s$ input parameter value 108 multiplied by the $dv_s/dt$ input parameter value 106, may be considered to decouple the negative state feedback of mass flow out of the second tank 16 as discussed above with reference to FIG. 5C.

The flow$_1$ and flow$_2$ state feedback controller with command feed forward 250, 252 may be said to provide yet another level of removal from the system parameters $dv_{in}/dt$ and $dm_{in}/dt$ directly associated with the states of the first and second actuators 18, 20, and provide the desired responsiveness to the parameters desired to be controlled.

It will be readily appreciated by one skilled in the art that portions of the control components described above may be combined, for example within a computer program implementing the functional blocks of the control components.

Figure 7:
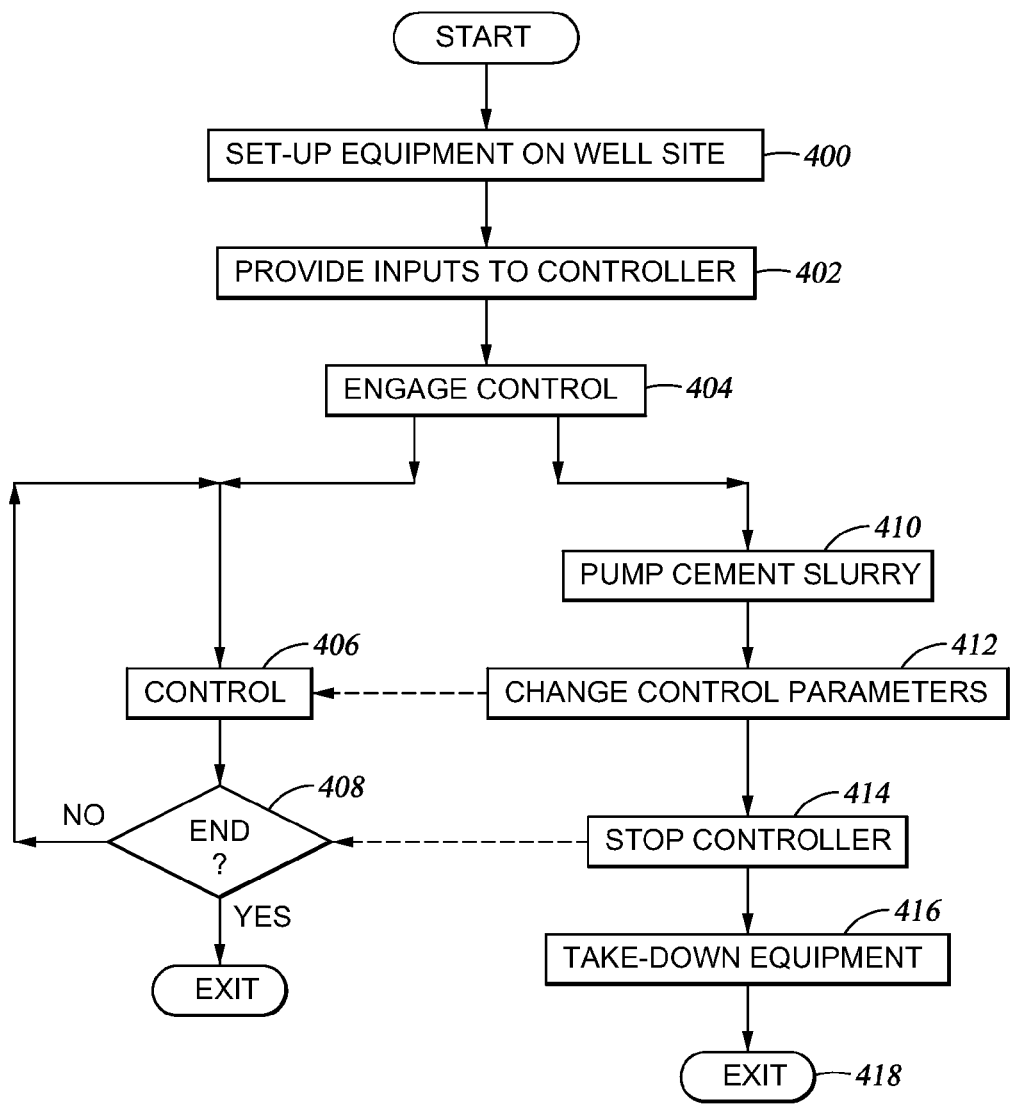
FIG. 7 is a flow diagram illustrating an exemplary use of the control system of FIG. 2.

In operation, as set out in the logic flow diagram of FIG. 7, the first control system 100 disclosed herein may, for example, be used to control a physical plant 10 comprising a cement slurry mixing system that provides cement slurry for cementing a tubular casing into a well bore. During such an operation, the operator may want the first control system 100 to provide a cement slurry having a desired density $\rho_s$, while pumping the cement slurry out of the second tank 16 at a desired volumetric flow rate $dv_s/dt$, and while maintaining the height of the cement slurry in the second tank 16 at a desired height $h_2$.

The process begins at block 400 in which the well bore servicing equipment, including the physical plant 10 and first control system 100, is brought to the well bore site and assembled. The discharge line 32 of FIG. 1 is coupled to the well bore, for example, using connected lengths of pipe, one end of which connects to a manifold or header at the well bore. Vessels containing blended dry cement and water in sufficient quantities are positioned to continuously supply the first feed line 28 and the second feed line 30 of FIG. 1.

Once the equipment has been set up at the well site, the process proceeds to block 402 where an operator provides input parameter values to the controller 102, for example through a console or lap top computer coupled to the controller 102, for example via a serial cable or a wireless link. The input parameter values may include the $h_2$ input 104, the $dv_s/dt$ input 106, and the $\rho_s$ input 108. In operation, the controller 102 will act to control the first and second actuators 18, 20, for example valves, such that the corresponding actual quantities of $\rho_s$, $dv_s/dt$, and $h_2$ approach or equal the input parameter values.

The process proceeds to block 404 where the operator engages the controller 102. The process continues hereinafter along two independent but at least partially coupled paths. Proceeding to block 406, the controller 102 actively controls the first and second actuators 18, 20 in accordance with the input parameter values and the sensed conditions of the physical plant 10. When the controller 102 is first engaged, it is likely that the first and second tanks 12, 16 will be empty. In this case, the controller 102 may open one of the first or second actuators 18, 20 fully open and then open the other of the first or the second actuators 18, 20 so as to achieve the desired cement slurry density as indicated by the $\rho_s$ input parameter value 108. The controller 102 continually determines and updates the actuator control signals that are output to the first and second actuators 18, 20, and the controller 102 may be said to be operating within a control loop represented by blocks 406 and 408. The controller 102 remains in this control loop 406, 408 while compensating for changes of indications returned from the physical plant 10, for example the sensed density $\rho_s$ of the cement slurry in the second tank 16 according to sensor 116, and for changes of input values, for example the $h_2$ input parameter value 104.

The process also concurrently proceeds along a second branch to block 410 where the physical plant 10 begins to pump cement slurry via the outflow pump 22, through the discharge line 32, through the coupled pipes, and downhole into the well bore. As the flow rate $dv_s/dt$ of the cement slurry exiting the second tank 16 via the outflow pump 22 changes, for example due to fluctuations in electrical power driving the outflow pump 22 or due to fluctuations in well bore back pressure, the controller 102 adjusts and maintains the actual physical parameters of the physical plant 10 to approach or equal the input parameter values.

The process proceeds to block 412 where the operator may modify an input parameter value, for example the $\rho_s$ input 108. This change causes the controller 102 to change the control signals that are output to the first and second actuators 18, 20 in the control loop 406, 408, for example by further opening the first actuator 18 and further closing the second actuator 20. The coupling between this action of modifying an input parameter value in block 412 and the control loop in blocks 406, 408 is indicated by a dotted line in FIG. 7.

The process proceeds to block 414 where the operator stops the controller 102. This action in block 414 will affect the control loop in blocks 406, 408 as indicated by a dashed line in FIG. 7. Specifically, stopping the controller 102 in block 414 causes the control loop in blocks 406, 408 to be exited. The process proceeds to block 416 where the physical plant 10 may be disconnected from the supply lines 28, 30 for water and dry cement, respectively, and the discharge line 32 may be disconnected from the pipes coupling the physical plant 10 to the well bore. The other equipment may be disassembled, the well bore may be closed in for a period to allow the cement to set, and the equipment of the physical plant 10 may be flushed and/or cleaned. The process exits at block 418.

In an embodiment, the indication of the height $h_1$ of the first mixture 13 in the first tank 12, and the indication of the height $h_2$ of the second mixture 15 in the second tank 16 are provided by two height observer components, which estimate rather than directly sense $h_1$ and $h_2$. In another embodiment, a single height observer may be employed to provide an indication of the height $h_2$ of the second mixture 15 in the second tank 16. In yet another embodiment, a single height observer may be employed to provide an indication of the height $h_1$ of the first mixture 13 in the first tank 12, for example in a physical plant 10 having only one tank.

Under field conditions, the height indications $h_1$, $h_2$ provided by the $h_1$ sensor 110 and the $h_2$ sensor 112 may be subject to various errors, for example height oscillations due to movement of the physical plant 10 onboard a floating platform or ship. Additionally, the stirring action of the first stirrer 24 and second stirrer 26 may significantly agitate the level surface of the first mixture 13 in the first tank 12 and of the second mixture 15 in the second tank 16, introducing variations in the height indications $h_1$ and $h_2$. The introduction of the first and second materials into the first tank 12, for example dry cement and/or water, may introduce further variations in the height indication $h_1$ provided by the $h_1$ sensor 110. All of these surface height variations may be analyzed as noise in the height signals. It may be desirable to employ estimated height indications of $h_1$ and $h_2$ rather than propagate the noise or oscillation that may be present in the indications of direct sensors, for example the $h_1$ sensor 110 and the $h_2$ sensor 112, into the controller 102.

Generally, a height observer is implemented as a dynamic control system to obtain an estimated height of the mixture in the tank in real time. First, this estimate of the mixture height is compared to the measured mixture height to obtain a height error. Then this mixture height error is used to drive the estimated mixture height to an actual mixture height through the use of a proportional-integral type controller, also referred to as a PI controller. By setting the gains of the PI controller, the noise and oscillations of the mixture in the tank can be substantially removed from the mixture height estimate while tracking the actual value of the mixture height. The height observer according to the present disclosure reduces the negative effects of noise and poor sensor performance due to environmental effects such as cement dust in the air or tank oscillations from the height readings. This height observer reflects the state of the actual mixture height with substantially no time lag.

Figure 8A:
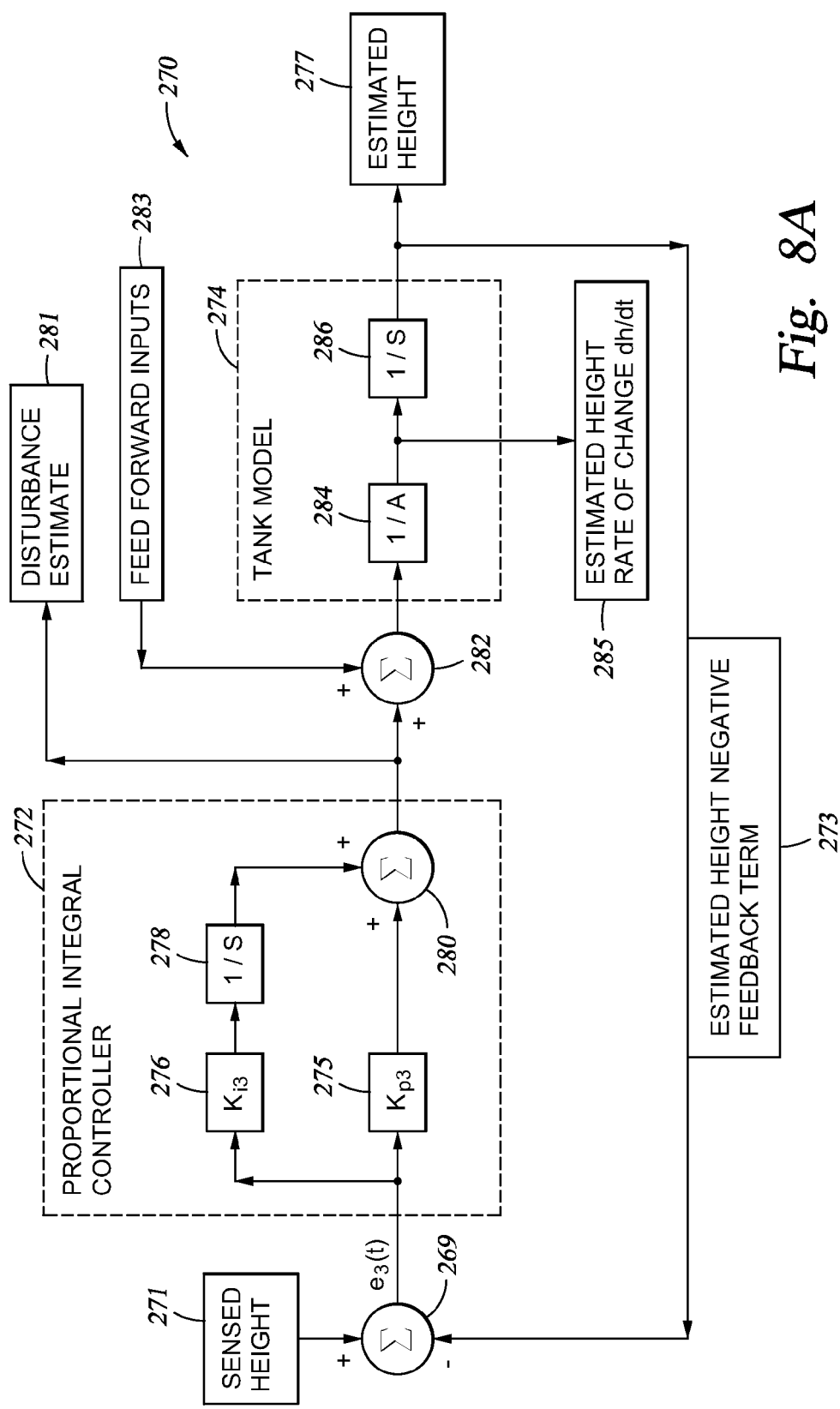
FIG. 8A is a block diagram of one embodiment of a height observer component.

Turning now to FIG. 8A, a block diagram depicts a general height observer 270. The height observer 270 includes a height PI controller component 272 and a height tank model component 274. An estimated height negative feedback term 273 is negatively summed by a fifth summation component 269 with a sensed height input 271 to determine a third error term $e_3(t)$. As shown in FIG. 8A, the estimated height negative feedback term 273 is the same signal as the final output produced by the general height observer 270, an estimated height 277, as described herein. While the value of the estimated height negative feedback term 273 and the estimated height 277 are the same, different labels are used herein to distinguish the different functions to which the signals are applied. The estimated height negative feedback term 273 is fed back into the height observer 270 as an input, thereby creating an estimating control loop, which yields a more accurate estimated height 277 each time through. The third error term $e_3(t)$ is processed by the height PI controller component 272 having a gain $K_{p3}$ for a third proportional component 275 and an integral gain $K_{i3}$ for a third integral component 276 associated with a third integration factor 278. The proportional and integral operations on the third error term $e_3(t)$ are then positively summed by a sixth summation component 280. The temporal response of the height PI controller component 272 to the third error term $e_3(t)$ input, represented by the function $u_3(t)$, may be expressed mathematically as:

$$u_3(t)=K_{p3}e_3(t)+K_{i3}\int e_3(t)dt \qquad (8)$$

The output of the height PI controller component 272 may be employed as an estimate of system errors, for example the difference between the desired and actual volumetric flow rates as well as other parameter estimations, for example the cross sectional area $A_1$ of the first tank 12. These errors may be collected and referred to as a disturbance, where the disturbance accounts for the discrepancies between what is demanded from the first control system 100 and what the first control system 100 actually produces, unmeasured quantities such as air flows into or out of the subject tank, and inaccuracies of estimates of system parameters. When the physical plant 10 mixes dry cement, there may be differences between the desired cement rate and the actual cement rate, because the cement delivery may be inconsistent. Differences between the desired cement rate and the actual cement rate may be accommodated by the disturbance. The output of the height PI controller component 272 may be referred to as a first disturbance estimate 281. The first disturbance estimate 281 may be fed back into the controller 102 to provide disturbance decoupling. Disturbance decoupling is described in more detail hereinafter.

The output of the height PI controller component 272 (i.e., the output from the sixth summation component 280) is positively summed by a seventh summation component 282 with one or more height feed forward inputs 283, for example volumetric flow rates such as the difference between the commanded volumetric flow rate $dv_{in}/dt$ into the first tank 12 and the volumetric flow rate $dv_{12}/dt$ of cement slurry out of the first tank 12 over the weir 14 into the second tank 16. The performance of the height observer 270 is expected to be improved by using height feed forward inputs 283 as compared to the performance of more traditional controllers, which only employ feedback terms with no feed forward inputs. Because the height of a mixture in a tank, for example the height $h_1$ of the first mixture 13 in the first tank 12, will increase or decrease due to a net positive or negative volumetric flow rate into the tank, the estimate of the height of the mixture in the tank depends upon the net positive or negative volumetric flow rate into the tank: the height feed forward inputs 283. The height feed forward inputs 283 may be summed either negatively or positively at the seventh summation component 282. The output of the seventh summation component 282 conforms to a volumetric flow rate that may be represented generally as dv/dt.

The height tank model component 274 multiplies the volumetric flow rate output of the seventh summation component 282 by a fourth integral component 284 associated with a fourth integration factor 286. The fourth integral component 284 corresponds to the inverse of the cross-sectional area of the tank, represented by "1/A" in the block for the fourth integral component 284. Multiplying a volumetric flow rate term (dv/dt) by the inverse of an area term, for example the inverse of a cross-sectional tank area expressed as 1/A, results in a velocity term (dx/dt), or more particularly in the case of a height controller, an estimated height rate of change dh/dt 285. The intermediate result of the estimated height rate of change dh/dt 285 may be used by other components in the controller 102, for example by the flow$_2$ state feedback controller with command feed forward 252.

Integrating the velocity term via the fourth integration factor 286 results in a displacement x, or in the present case a height h. Thus, the output of the height tank model component 274 is an estimated height 277 of the mixture in the tank. One skilled in the art will recognize that the results of the analysis of the height observer 270 above may be applied to digital signals as well as analog signals. For example, analog parameters such as the sensed height input 271 may be converted by an analog-to-digital converter (A/D converter) to a digital signal. Similarly, analog outputs may be produced by a digital-to-analog converter (D/A converter), optionally combined with an amplifier to provide sufficient power to drive an electromechanical device, converting a digital control signal to an analog control signal suitable for controlling the first actuator 18 and the second actuator 20. Height observers, such as the height observer 270, are further disclosed in related U.S. patent application Ser. No. 11/029,072, entitled "Methods and Systems for Estimating a Nominal Height or Quantity of a Fluid in a Mixing Tank While Reducing Noise," filed Jan. 4, 2005, which is incorporated herein by reference for all purposes.

Figure 8B:
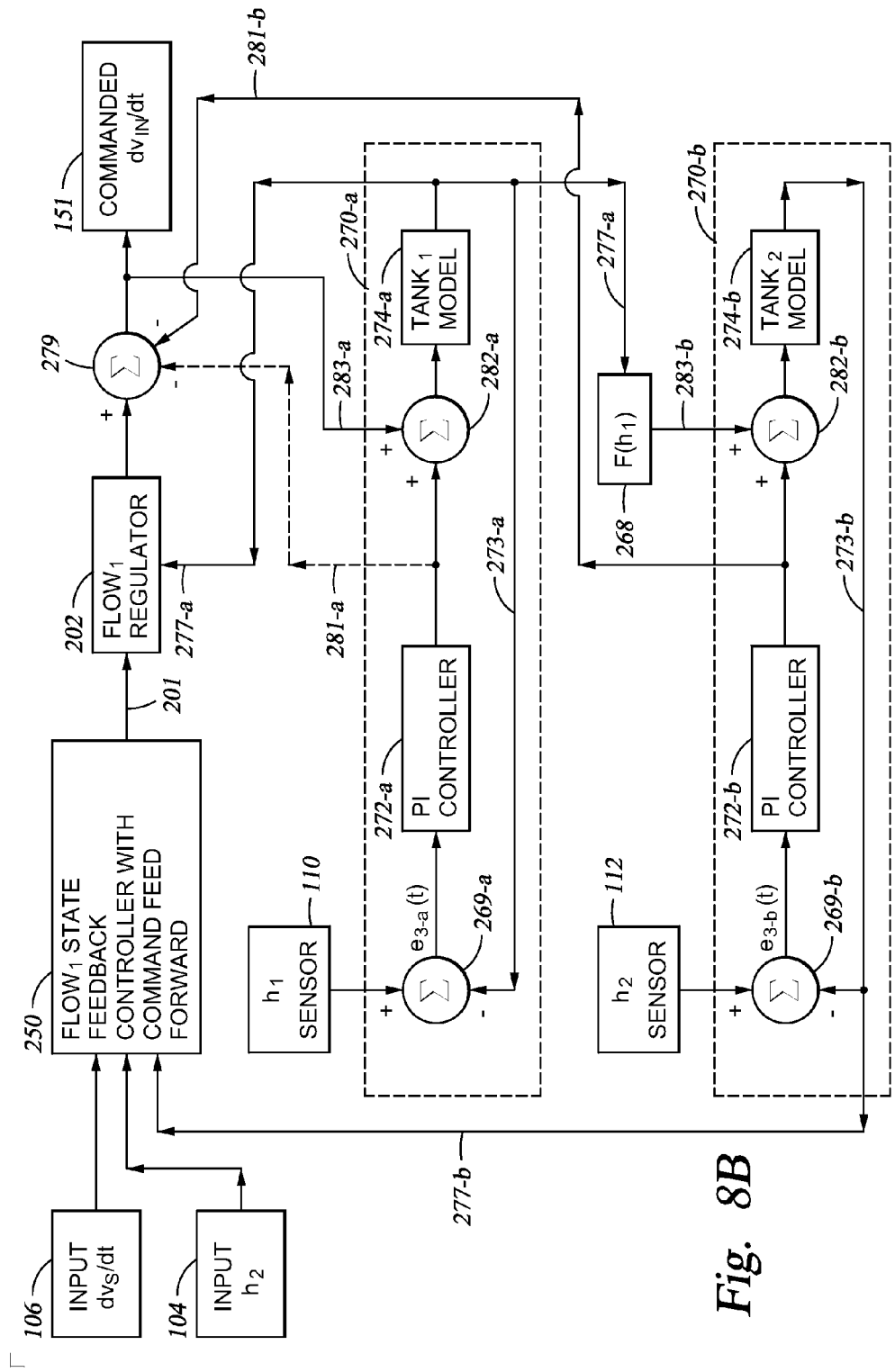
FIG. 8B is a block diagram of one embodiment of a control system comprising first and second height observer components.

Turning now to FIG. 8B, a block diagram shows a portion of one embodiment of the first control system 100 depicted in FIG. 2 and FIG. 6, incorporating a first height observer 270-*a* and a second height observer 270-*b* rather than directly using the $h_1$ sensor 110 and the $h_2$ sensor 112. In the embodiment depicted in FIG. 8B, the $h_1$ sensor 110 provides an indication of the height $h_1$ of the first mixture 13 in the first tank 12 to the first height observer 270-*a*, which is negatively summed by a ninth summation component 269-*a* with a first estimated height negative feedback term 273-*a* of the first mixture 13 in the first tank 12 to obtain an error term $e_{3\text{-}a}(t)$ that is fed into a first height PI controller component 272-*a*. The output of the first height PI controller component 272-*a* is positively summed by a tenth summation component 282-*a* with a height feed forward input 283-*a* from an eleventh summation component 279, and the output of the tenth summation component 282-*a* is processed by a first height tank model component 274-*a* to produce an estimated height 277-*a* of the first mixture 13 in the first tank 12. The first proportional factor 284 (i.e., 1/A) for the first height tank model component 274-*a* employs the cross-sectional area $A_1$ of the first tank 12. The estimated height 277-*a* of the first mixture 13 in the first tank 12, which may be referred to as an indication of the height of the first mixture in the first tank 12, is output to the first flow regulator 202 and also to the second height observer 270-*b*. Note that the estimated height 277-*a* and the first estimated height negative feedback term 273-*a* are the same signals but are identified by different labels to point out their different functions in the controller 102. The output from the first height PI controller component 272-*a*, as a first disturbance estimate signal 281-*a*, optionally may be negatively summed with the output of the first flow regulator 202 by the eleventh summation component 279 to provide disturbance decoupling to the determination of the commanded volumetric flow rate $dv_{in}/dt$ of material into the first tank 12. In another embodiment, disturbance decoupling is provided by a second disturbance estimate signal 281-*b* that is negatively summed with the output of the first flow regulator 202 by the eleventh summation component 279. The second disturbance estimate signal 281-*b* is determined by the second height observer 270-*b*, as discussed in more detail below. The commanded volumetric flow rate $dv_{in}/dt$ output by the eleventh summation component 279 is the commanded first volume flow rate $dv_{in}/dt$ signal 151 to the flow modulator 150 or to the first and second flow modulators 152, 154 as described above with reference to FIG. 3.

The $h_2$ sensor 112 provides an indication of the height $h_2$ of the second mixture 15 in the second tank 16 to the second height observer 270-*b*, which is negatively summed by a twelfth summation component 269-*b* with a second estimated height negative feedback term 273-*b* of the second mixture 15 in the second tank 16 to obtain an error term $e_{3\text{-}b}(t)$ that is fed into a second height PI controller component 272-*b*. The output of the second height PI controller component 272-*b* is positively summed by a thirteenth summation component 282-*b* with a second height feed forward input 283-*b* output by a first calculation component 268. The first calculation component 268 outputs the result of the function $F(h_1)$ based on the estimated height 277-*a* of the first mixture 13 in the first tank 12. In an embodiment, the value of $F(h_1)$ is calculated by the first flow regulator 202 and provided to the thirteenth summation component 282-*b* as the second height feed forward input 283-*b*. In this embodiment, the first calculation component 268 is not employed. The output of the thirteenth summation component 282-*b* is then processed by a second height tank model component 274-*b* to produce a second estimated height 277-*b* of the second mixture 15 in the second tank 16. The first proportional factor 284 (i.e., 1/A) for the second height tank model component 274-*b* employs the cross-sectional area $A_2$ of the second tank 16. Note that the second estimated height 277-*b* and the second estimated height negative feedback term 273-*b* are the same signals but are identified by different labels to point out their different functions in the controller 102.

Within the second height observer 270-*b*, the output from the second height PI controller component 272-*b* provides the second disturbance estimate signal 281-*b* that is negatively summed by the eleventh summation component 279, as previously discussed. In an embodiment, the second disturbance estimate signal 281-*b* may provide a more accurate estimate of the volumetric rate disturbance in the system 100 as compared to the first disturbance estimate signal 281-*a* because the height of the second mixture 15 in the second tank 16 varies more than the height of the first mixture 13 in the first tank 12. Additionally, in the two tank system of FIG. 1, the surface of the first mixture 13 in the first tank 12 may not be level but may slope downwardly from the point where the actuators 18, 20 dispense the materials to the weir 14. The second estimated height 277-*b* of the second mixture 15 in the second tank 16, which may be referred to as an indication of the height $h_2$ of the second mixture 15 in the second tank 16, is fed into the flow$_1$ state feedback controller with command feed forward 250 as an input, and the control process is repeated. The estimated height rate of change dh/dt 277 of the second height observer 270-*b*, $dh_2/dt$, is used for state feedback decoupling by the flow$_2$ state feedback controller with command feed forward 252.

The advantages of the height observer 270, such as, for example, attenuation of noise and improvement of poor sensor performance, estimation of a disturbance term, and estimation of a parameter rate of change, may be obtained in a density observer having a structure related to the height observer 270. In an embodiment, the indication of the density $\rho_{12}$ of the first mixture 13 in the first tank 12 and the indication of the density $\rho_s$ of the second mixture 15 in the second tank 16 are provided by two density observer components which estimate rather than directly sense the densities $\rho_{12}, \rho_s$ of the mixtures 13, 15, respectively. In another embodiment, the density observer may be used to estimate the density of other mixtures or materials in systems other than the physical plant 10 depicted in FIG. 1.

Figure 9A:
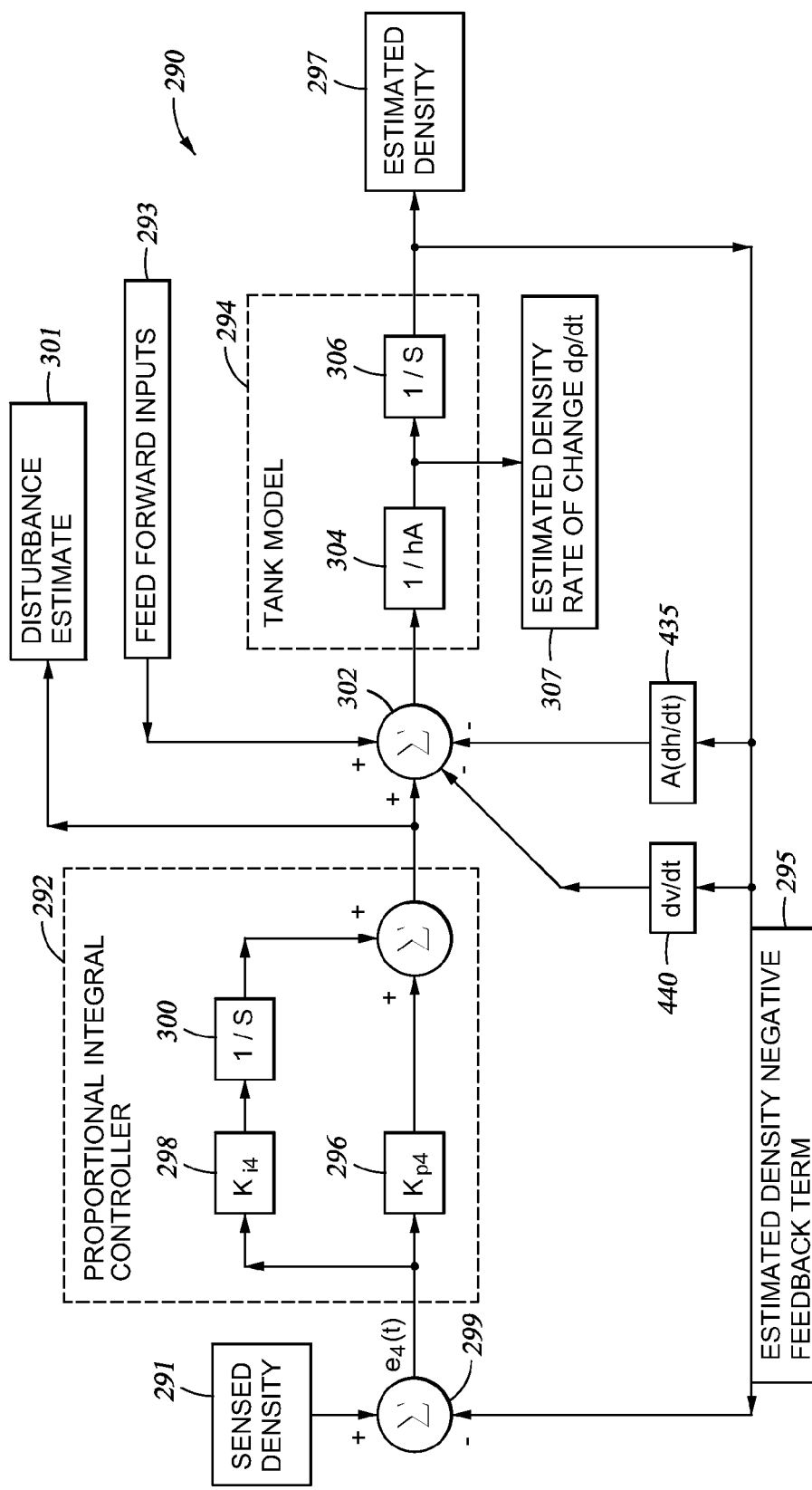
FIG. 9A is a block diagram of one embodiment of a density observer component.

Turning now to FIG. 9A, a general density observer 290 operable to determine an estimated density of a mixture in a tank is depicted. The density observer 290 includes a density PI controller component 292 and a density tank model component 294. An eighth summation component 299 negatively sums an estimated density negative feedback term 295 with a sensed density input 291 to determine a fourth error term $e_4(t)$. The fourth error term $e_4(t)$ is processed by the density PI controller component 292, which has a gain $K_{p4}$ for a fourth proportional component 296 and an integral gain $K_{i4}$ for a fifth integral component 298 associated with a fifth integration factor 300. In an embodiment, the fourth error term $e_4(t)$ may be processed by a filter instead of by the density PI controller component 292, such as an analog filter or a digital filter, to introduce desirable time lags or to attenuate and/or amplify certain frequency components of the fourth error term $e_4(t)$.

The output of the density PI controller component 292 may be employed as an estimate of system errors, for example the difference between the desired and actual mass flow rates as well as other parameter estimations. These errors may be collected and referred to as a disturbance, where the disturbance accounts for the discrepancies between what is demanded from the first control system 100 and what the first control system 100 actually produces, unmeasured quantities such as air flows into or out of the subject tank, and inaccuracies of estimates of system parameters. The output of the density PI controller component 292 may be referred to as a second disturbance estimate 301. The second disturbance estimate 301 may be fed back into the controller 102 to provide disturbance decoupling. Disturbance decoupling is described in more detail hereinafter.

The output of the density PI controller component 292, which conforms to a mass flow rate, is summed with one or more density feed forward inputs 293, for example a mass flow rate, such as the difference between the commanded mass flow rate into the first tank 12 and the mass flow rate of cement slurry out of the first tank 12 over the weir 14 into the second tank 16, by a third summation component 302. The output of a twelfth multiplication component 435 and the output of a thirteenth multiplication component 440 are also negatively summed by the third summation component 302. Generally, the density feed forward inputs 293 are associated with mass flow into the associated tank and the outputs of the twelfth and thirteenth multiplication components 435, 440 are associated with mass flow out of the associated tank. The output of the third summation component 302 is processed by the density tank model component 294. The density tank model component 294 multiplies the output of the third summation component 302 by a sixth integral component 304 associated with a sixth integration factor 306. The sixth integral component 304 is inversely proportional to the height of the mixture times the cross-sectional area of the tank, as represented by "1/hA" in the block for the sixth integral component 304. Note that dividing a mass flow rate by hA is substantially equivalent to dividing through by the volume of the tank resulting in an estimated density rate of change 307 dρ/dt. The height may be provided by a height sensor, for example the $h_1$ sensor 110, or the height observer 270. Alternatively, the height may be a fixed constant determined by experimentation to provide a preferred response rate of the general density observer 290. Integrating this quotient with respect to time results in a density. The output of the density tank model component 294 is thus the estimated density 297 of the mixture in the tank. The estimated density negative feedback term 295 is the same signal as the estimated density 297, but the estimated density feedback term 295 is fed back into the eighth summation component 299 at the input to the density observer 290 to be processed through the PI controller 292 and tank model component 294 to yield a more accurate estimated density 297 each time through. The estimated density negative feedback term 295 is multiplied by a factor A(dh/dt) by the twelfth multiplication component 435 to produce a ρA(dh/dt) term that is negatively fed back to the third summation component 302 as described above. The ρA(dh/dt) term corresponds to a mass rate of change based on changes in the height of the mixture in the tank. The dh/dt factor may be determined from a height sensor or a height observer. Alternatively, in an embodiment of the system 100 that provides no indication or estimate of height of the mixture, the twelfth multiplication 435 may be absent from the general density observer 290. The estimated density negative feedback term 295 is also multiplied by a factor dv/dt by the thirteenth multiplier component 440 to produce a ρ(dv/dt) term that is negatively fed back to the third summation component 302 as described above. The ρ(dv/dt) term corresponds to a mass rate of change due to flow of the mixture out of the tank. In an embodiment, the sensed density input 291 may be provided by a density sensor, for example the $\rho_{12}$ sensor 114, installed in a recirculation line or an outflow line, such as the discharge line 32, associated with the tank. Thus, the density of the mixture as measured in the recirculation line may lag several seconds behind the density of the mixture in the tank. In this embodiment, a time delay of several seconds, such as three seconds, for example, may be introduced in the estimated density negative feedback term 295 before negatively summing with the sensed density 291 at the eighth summation component 299 to determine the fourth error term $e_4(t)$. This allows the sensed and estimated density to be in the same time reference frame before determining the fourth error term $e_4(t)$. The appropriate time delay may be readily determined from experimentation by one skilled in the art and depends upon the viscosity of the mixture and the speed of mixing.

Because the structures of the height observer 270 and the density observer 290 are related, one skilled in the art need only determine the gains appropriate to the height observer 270, determine the gains appropriate to the density observer 290, and configure the two observer structures 270, 290 accordingly. One skilled in the art will recognize that the results of the analysis of the density observer 290 above may be applied to digital signals as well as analog signals. For example, analog parameters such as the indication of density $\rho_s$ of the second mixture 15 in the second tank 16 from the $\rho_s$ sensor 116 may be converted by an analog-to-digital converter (A/D converter) to a digital signal. Similarly, analog outputs may be produced by a digital-to-analog converter (D/A converter), optionally combined with an amplifier to provide sufficient power to drive an electromechanical device, converting a digital control signal to an analog control signal suitable for controlling the first actuator 18 and the second actuator 20.

Figure 9B:
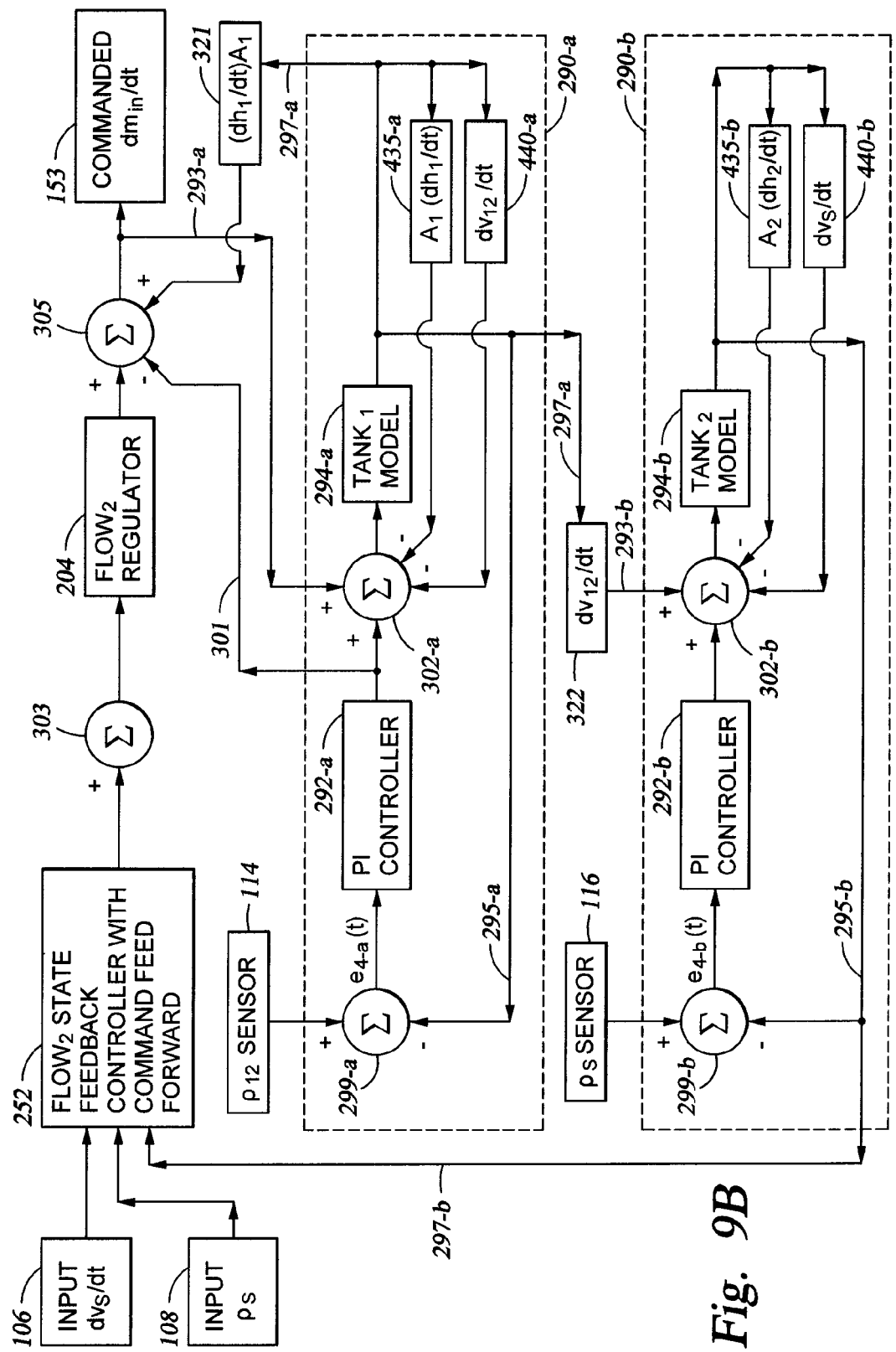
FIG. 9B is a block diagram of one embodiment of a control system comprising first and second density observer components.

Turning now to FIG. 9B, a block diagram shows a portion of one embodiment of the first control system 100 incorporating a first density observer 290-a and a second density observer 290-b. The $\rho_{12}$ sensor 114 provides an indication of the density $\rho_{12}$ of the first mixture 13 in the first tank 12 to the first density observer 290-a, which is negatively summed by a fourteenth summation component 299-a with a first estimated density negative feedback term 295-a of the first mixture 13 in the first tank 12 to obtain an error term $e_{4-a}(t)$. As described above, in an embodiment where the $\rho_{12}$ sensor 114 is located in a recirculation line, the estimated density negative feedback term 295-a may be delayed several seconds before it is input to the fourteenth summation component 299-a. The $e_{4-a}(t)$ error term is fed into a first density PI controller component 292-a. The output of the first density PI controller component 292-a is positively summed with a first density feed forward input 293-a from a seventeenth summation component 305 by a fifteenth summation component 302-a. The output of a fourteenth multiplication component 435-a and a fifteenth multiplication component 440-a, corresponding to a mass rate of change due to changes in height in the first tank 12 and the mass flow rate out of the first tank 12, respectively, are negatively summed by the fifteenth summation component 302-a The sum output by the fifteenth summation component 302-a is processed by a first density tank model component 294-a. Note that the sixth integral component 304 for the first density tank model component 294-a employs the cross sectional area $A_1$ of the first tank 12 and the height $h_1$ of the first mixture 13 in the first tank 12. Note that the first estimated density negative feedback term 295-a and a first estimated density 297-*a* are the same signals but are identified by different labels to point out their different functions in the controller 102.

The output from the first density P1 controller component 292-*a*, as the second disturbance estimate 301, is negatively summed by the seventeenth summation component 305 with the output from the second flow regulator 204 plus the output generated by a fifth multiplier component 321 to determine the commanded first mass flow rate $dm_{in}/dt$ signal 153. The second disturbance estimate 301 provides disturbance decoupling to the determination of the commanded first mass flow rate $dm_{in}/dt$ signal 153, while the fifth multiplier component 321 provides state feedback decoupling. The fifth multiplier component 321 outputs the product formed by multiplying the first estimated density 297-*a* of the first mixture 13 in the first tank 12 by the height rate of change $dh_1/dt$ of the first mixture 13 in the first tank 12 and by the area $A_1$ of the first tank 12, obtaining the height rate of change $dh_1/dt$, for example, from the estimated height rate of change 285 output of the first height observer 270*a*. In another embodiment, the second disturbance estimate 301 may be provided by the second density observer 290-*b*.

To estimate the density $\rho_s$ of the second mixture 15, the $\rho_s$ sensor 116 provides an indication of the density $\rho_s$ of the second mixture 15 in the second tank 16 to the second density observer 290-*b*. This indication of $\rho_s$ is summed by an eighteenth summation component 299-*b* with a second estimated density negative feedback 295-*b* of the second mixture 15 in the second tank 16 to obtain an error term $e_{4-b}(t)$. As described above, in an embodiment where the $\rho_s$ sensor 116 is located in a recirculation line or in an outflow line, such as the discharge line 32, the estimated density negative feedback term 295-*b* may be delayed several seconds before it is input to the eighteenth summation component 299-*b*. The error term $e_{4-b}(t)$ is fed into a second density PI controller component 292-*b*. A second density feed forward input 293-*b*, output by a sixth multiplier component 322, is positively summed by a nineteenth summation component 302-*b* with the output of the second density PI controller component 292-*b*. The sixth multiplier component 322 outputs the product formed by multiplying the first estimated density 297-*a* of the first mixture 13 in the first tank 12 by the volumetric flow rate $dv_{12}/dt$ of the first mixture 13 into the second tank 16. The output of a sixteenth multiplication component 435-*b* and a seventeenth multiplication component 440-*b*, corresponding to a mass rate of change due to changes in height in the second tank 16 and mass flow rate out of the second tank 16, respectively, are negatively summed by the nineteenth summation component 302-*b*. The output of the nineteenth summation component 302-*b* is processed by a second density tank model component 294-*b*. Note that the sixth integral component 304 for the second density tank model component 294-*b* employs the cross sectional area $A_2$ of the second tank 16 and the height $h_2$ of the second mixture 15 in the second tank 16. The second estimated density 297-*b* of the second mixture 15 in the second tank 16 is provided as an input to the $flow_2$ state feedback controller with command feed forward 252 for use in generating the commanded mass flow rate $dm_{12}/dt$, which is the commanded mass flow rate $dm_{12}/dt$ signal 203 provided as a commanded parameter value to the second flow regulator 204 as described above with reference to FIG. 4. Note that the second estimated density negative feedback term 295-*b* and the second estimated density 297-*b* are the same signals but are identified by different labels to point out their different functions in the controller 102.

One skilled in the art will readily appreciate that the components of the first control system 100 disclosed above are susceptible to many alternate embodiments. While several alternate embodiments are disclosed hereinafter, other embodiments are contemplated by the present disclosure.

Figure 10A:
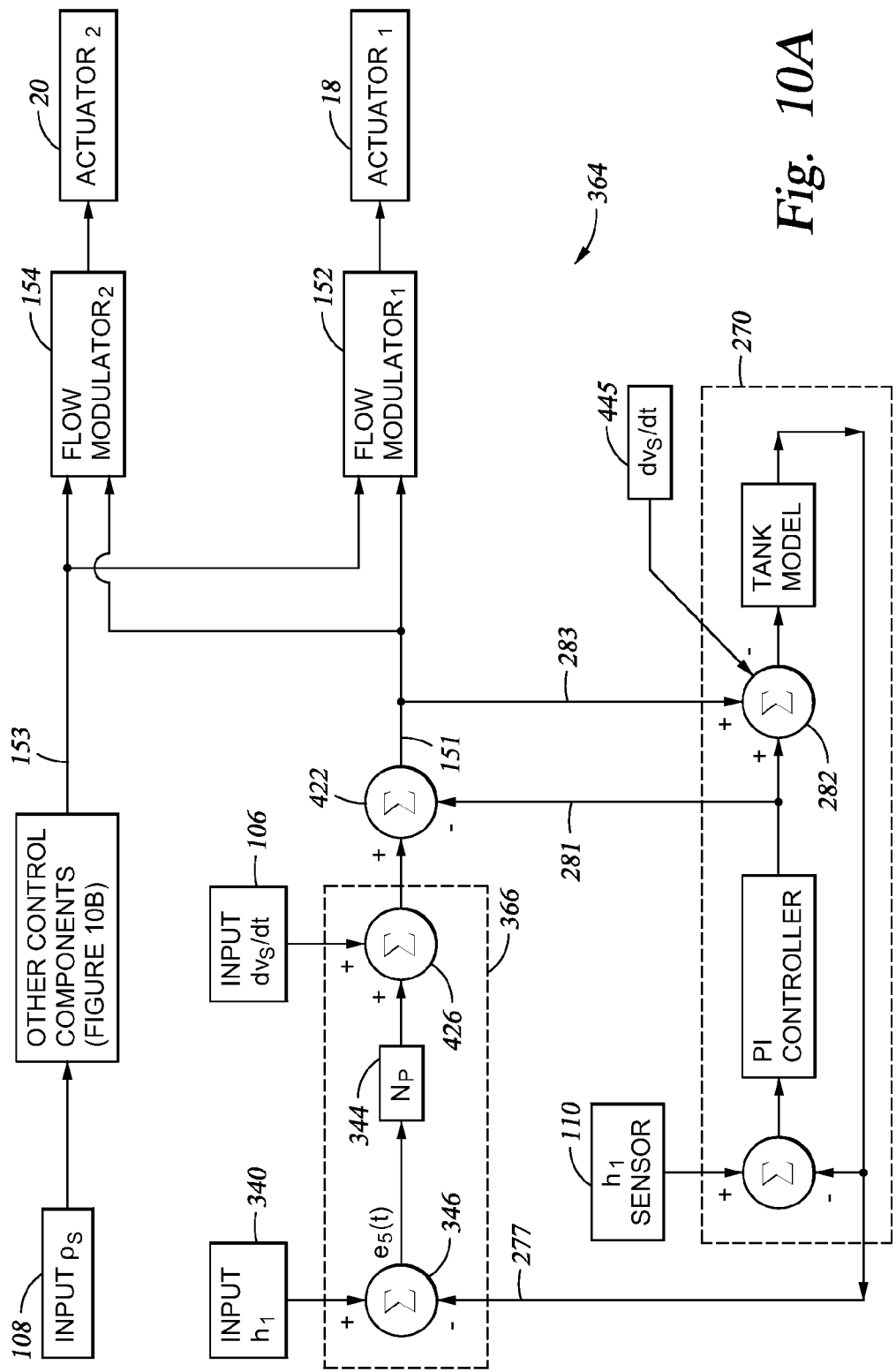
FIG. 10A is a block diagram of a first portion of an embodiment of a control system for a physical plant having a single tank, the first portion including a height controller.

Turning now to FIG. 10A, a portion of a second control system 364 is depicted. The second control system 364 controls a physical plant 10 having a single tank, such as the first tank 12 of FIG. 1, and first and second actuators 18, 20. The second control system 364 uses a height observer 270, which is substantially similar to that described above with respect to FIG. 8A, to estimate the height of the first mixture 13 in the first tank 12 and to determine the first disturbance estimate 281.

Several components are combined to provide a first height controller 366 that is substantially similar to the $flow_1$ state feedback controller with command feed forward 250 described above with reference to FIG. 5B. Specifically, an eighteenth summation component 346 determines a fifth error term $e_5(t)$ by negatively summing the estimated height 277 produced by the height observer 270 with an $h_1$ input 340, provided for example by an operator. The fifth error term $e_5(t)$ is processed by a proportional gain term $N_p$ in a seventh multiplication component 344. A thirtieth summation component 426 sums the output of the seventh multiplication component 344 positively with the $dv_s/dt$ input 106 that provides command feed forward. A twenty-eighth summation component 422 negatively sums the first disturbance estimate 281 with the output of the thirtieth summation component 426. The twenty-eighth summation component 422 provides the same function as the $flow_1$ regulator 202 as described above with reference to FIG. 8B. The output of the twenty-eighth summation component 422 is the commanded first volume flow rate $dv_{in}/dt$ signal 151 that is fed to the first and second flow modulators 152, 154 and into the seventh summation component 282 of the height observer 270 as the volume feed forward inputs 283. A first $dv_s/dt$ term 445 is fed negatively into the seventh summation component 282, and the first $dv_s/dt$ term 445 may be obtained either from a flow sensor or may be based on the $dv_s/dt$ input 106. The first flow modulator 152 controls the first actuator 18 based on the commanded first volume flow rate $dv_{in}/dt$ signal 151 and the commanded first mass flow rate $dm_{in}/dt$ signal 153, which is generated as described below with reference to FIG. 10B.

Figure 10B:
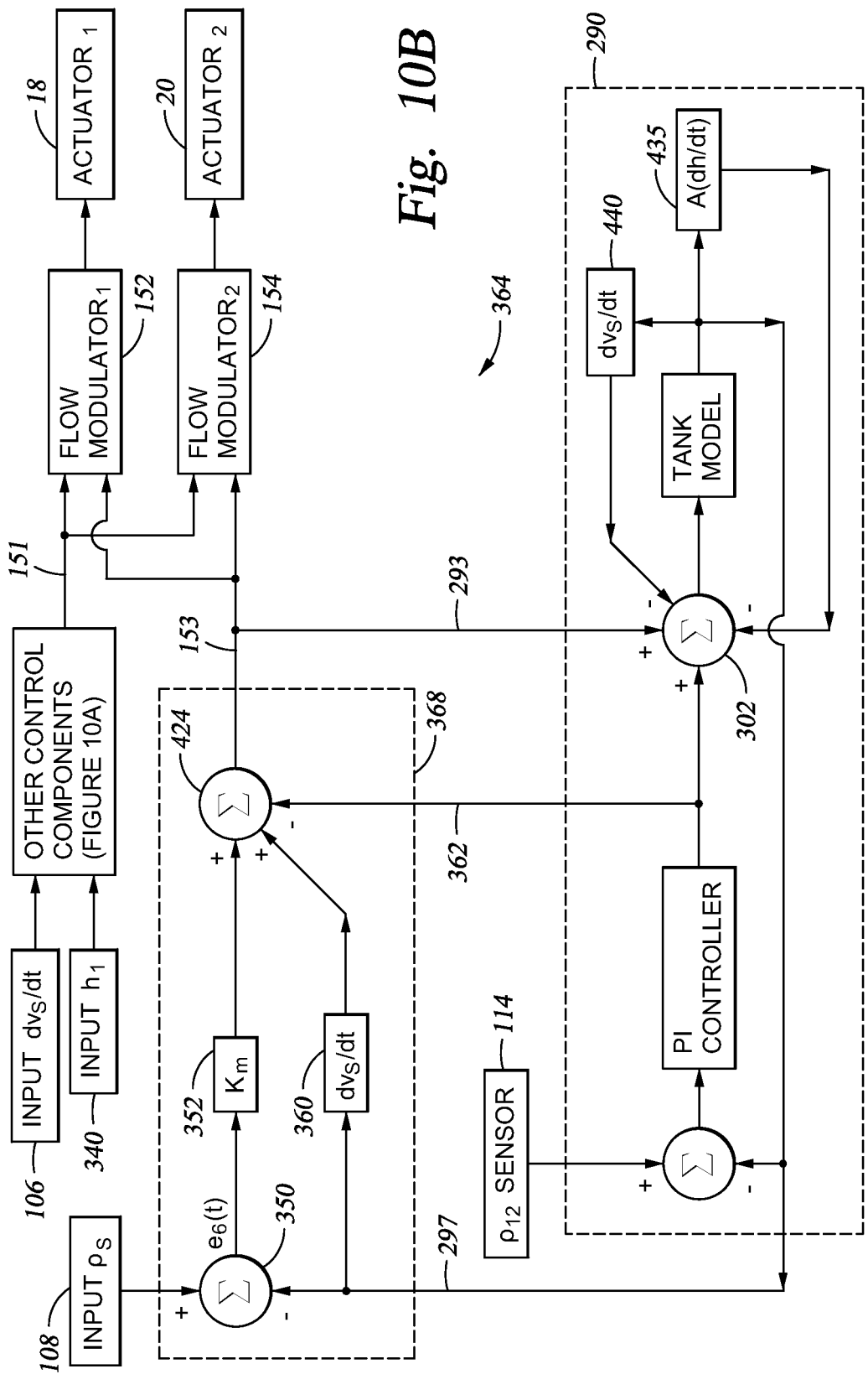
FIG. 10B is a block diagram of a second portion of the embodiment of the control system for a physical plant having a single tank, the second portion including a density controller.

Turning now to FIG. 10B, another portion of the second control system 364 is depicted. Several components are combined to provide a first density controller 368 that is substantially similar to the $flow_2$ state feedback controller with command feed forward 252 described above with reference to FIG. 5C, with the exception that the $(dh_2/dt)A_2$ term associated with the first multiplication component 266 is omitted, because there is no second tank 16 in this embodiment. A twentieth summation component 350 determines a sixth error term $e_6(t)$ by negatively summing the density estimate 297 produced by the modified density observer 356 with the input $\rho_s$ 108. The sixth error term $e_6(t)$ is processed by a proportional gain term $K_m$ in a ninth multiplication component 352. A tenth multiplication component 360 multiplies the density estimate 297 by the $dv_s/dt$ input 106. The second disturbance estimate 362 is negatively summed with the outputs of the ninth and tenth multiplication components 352, 360 by a twenty-ninth summation component 424. The output of the tenth multiplication component 360 may be considered to provide command feed forward to a density controller 368 that comprises the twentieth summation component 350, the ninth multiplication component 352, the tenth multiplication component 360, and the twenty-ninth summation component 424. The output of the twenty-ninth summation component 424 is the commanded first mass flow rate $dm_{in}/dt$ signal 153 that is fed into the first and second flow modulators 152, 154 and into the density observer 290 as the density feed forward inputs 293. The second flow modulator 154 controls the second actuator 20 based on the commanded first volume flow rate $dv_{in}/dt$ signal 151 and the commanded first mass flow rate $dm_{in}/dt$ signal 153, which is generated as described above with reference to FIG. 10A.

One of ordinary skill in the art will readily appreciate that no integral processing is employed in the first height controller 366 described above with reference to FIG. 10A or in the density controller 368 because the effect of command feed forward and disturbance decoupling is to reduce steady-state error to substantially zero, thereby transforming the second control system 364 from a first order non-linear system (as in the first control system 100), to a first order linear system that may be controlled by proportional controllers. In general, if the disturbances are decoupled or removed using the observers, for example by the height observer 270 and/or the density observer 290, and the command feed forward terms, then a proportional (P) controller may be used with substantially zero steady state error, since the second control system 364 will behave in accordance with a linear first order differential equation. If the disturbances are not decoupled, it may be preferable to use a PI controller, so that the integral term acts to ensure substantially zero steady state error.

Figure 11:
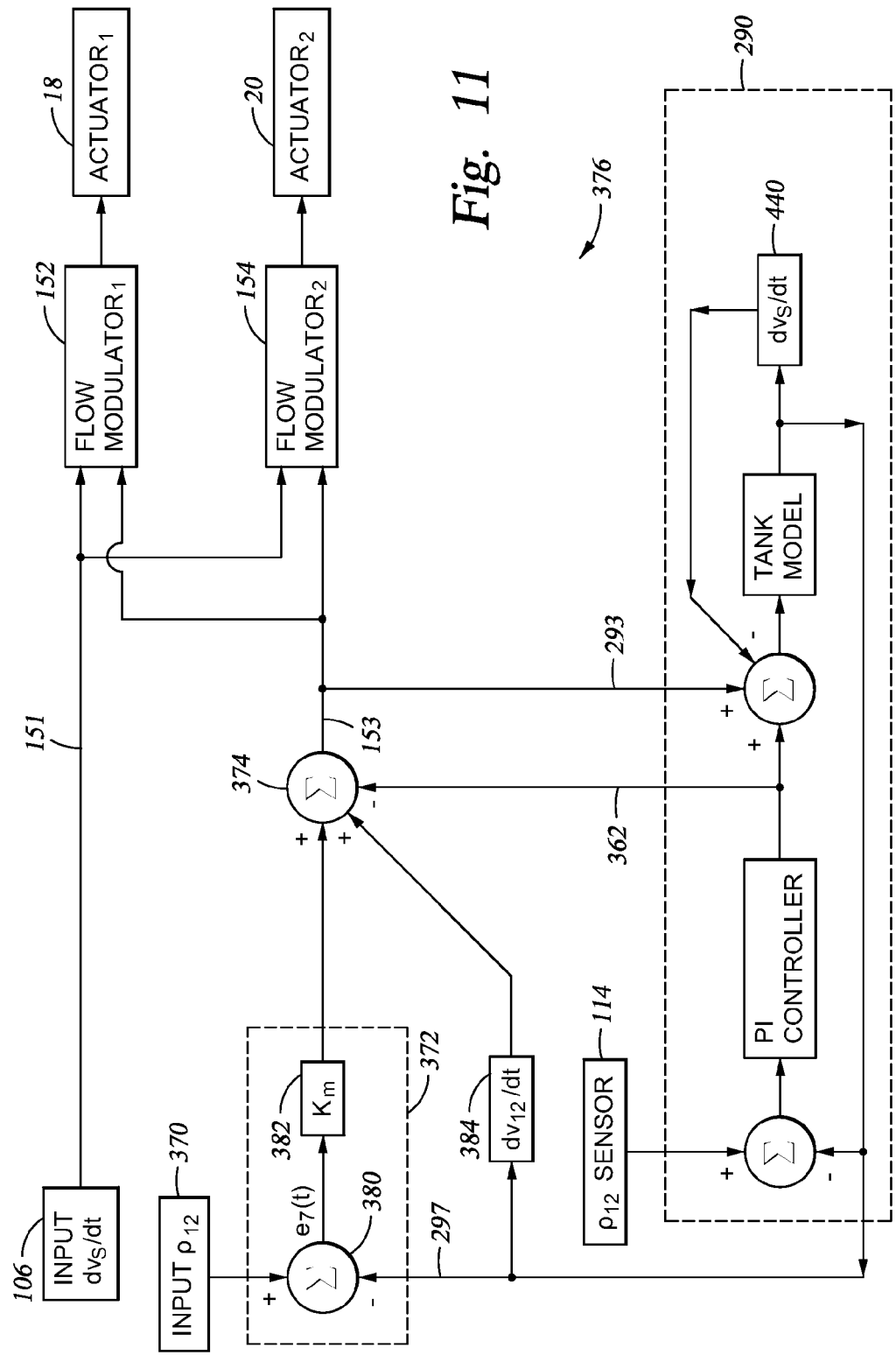
FIG. 11 is a block diagram of one embodiment of a control system having a density observer associated with a first tank and no automated height control.

Turning now to FIG. 11, a third control system 376 is depicted. The third control system 376 controls a physical plant 10 having two actuators 18, 20; two tanks 12, 16; and only a single sensor, the $\rho_{12}$ sensor 114, measuring the density $\rho_{12}$ of the first mixture 13 in the first tank 12. In this embodiment, the commanded first volume flow rate $dv_{in}/dt$ signal 151 to the first and second flow modulators 152, 154 is provided directly by the $dv_s/dt$ input 106 without employing a flow regulator or other components as in the first control system 100. Also, this embodiment contains no height controller, so an operator may adjust the actual volumetric flow rate $dv_s/dt$ out of the second tank 16 by controlling the outflow pump 22, and thereby maintain the desired height $h_2$ of the second mixture 15 in the second tank 16.

The density observer 290 determines the density estimate 297 of the density $\rho_{12}$ of the first mixture 13 in the first tank 12 and the second disturbance estimate 362 based on the output of the $\rho_{12}$ sensor 114 and density feed forward inputs 293. Because this embodiment provides no indication of height, the A(dh/dt) term in FIG. 9A that is associated with the twelfth multiplier component 435 is omitted. As described above with reference to FIG. 9A, in the present embodiment the height component of the sixteenth integral component 304 is a constant value chosen to provide a desirable system response time. A twenty-second summation component 380 negatively sums the density estimate 297 with a $\rho_{12}$ input parameter value 370 to determine a seventh error term $e_7(t)$, which is multiplied by a proportional gain $K_m$ by an eleventh multiplication component 382. The $\rho_{12}$ input 370, for example, may be provided by an operator through an interface. The twenty-second summation component 380 and the eleventh multiplication component 382 comprise a second density controller 372 that controls the density $\rho_{12}$ of the first mixture 13 in the first tank 12. In steady state conditions, the density of the second mixture 15 in the second tank 16 will follow the controlled density $\rho_{12}$ of the first mixture 13 in the first tank 12. When the $\rho_{12}$ input 370 is changed, the density $\rho_s$ of the second mixture 15 in the second tank 16 will substantially equal the density $\rho_{12}$ of the first mixture 13 in the first tank 12 after a time lag.

A twelfth multiplication component 384 multiplies the density estimate 297 by the approximate actual volumetric flow $dv_{12}/dt$. Because $h_1$ is not measured, and the function $F(h_1)$ may not be used, the $dv_s/dt$ input 106 is used to approximate the actual volumetric flow $dv_{12}/dt$ over the weir 14. The output of the twelfth multiplication component 384 provides state feedback decoupling to the control system 376 to compensate for mass leaving the first tank 12.

The second disturbance estimate 362 is negatively summed with the output of the eleventh and twelfth multiplication components 382, 384 by a twenty-first summation component 374 to determine the commanded first mass flow rate $dm_{in}/dt$ signal 153. The commanded first mass flow rate $dm_{in}/dt$ signal 153 is provided to the first and second flow modulators 152, 154 to control the first and second actuators 18, 20 as described above. The output of the twenty-first summation component 374 also provides the density feed forward inputs 293 to the density observer 290.

Figure 12:
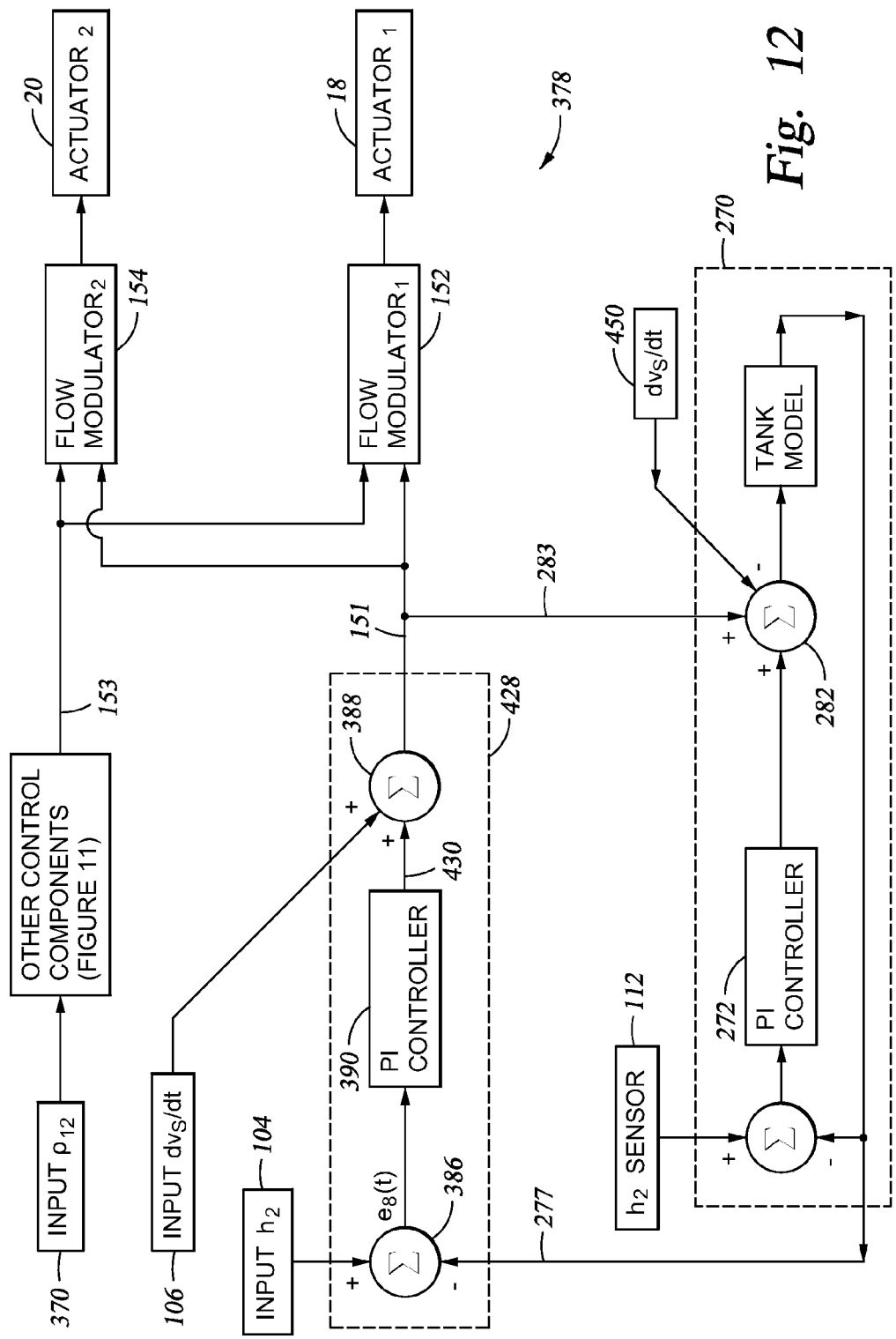
FIG. 12 is a block diagram of one embodiment of a control system having a density observer associated with the first tank and a height observer associated with a second tank.

Turning now to FIG. 12, a fourth control system 378 is depicted. The fourth control system 378 is substantially similar to the third control system 376, with the exception that the fourth control system 378 includes the height observer 270 and a second height controller 428. The height observer 270 determines the estimated height 277 of the second mixture 15 in the second tank 16 based on input from the $h_2$ sensor 112 and the height feed forward inputs 283. A second $dv_s/dt$ factor 450 is negatively summed with the height feed forward inputs 283 and the output of the height PI controller 272 by the seventh summation component 282. The estimated height 277 is negatively summed with the $h_2$ input 104 by a twenty-third summation component 386 to generate an eighth error term $e_8(t)$. The eighth error term $e8(t)$ is processed by a third PI controller 390 to produce a commanded height signal 430, which is summed with the $dv_s/dt$ input 106 by a twenty-fourth summation component 388 to produce the $dv_{in}/dt$ signal 151 provided to the flow modulators 152, 154. Based on the $dv_{in}/dt$ signal 151 and the $dm_{in}/dt$ signal 153, the first and second flow modulators 152, 154 control the states of the first and second actuators 18, 20 as described above.

While the physical plant 10 controlled by the several embodiments of the control systems 100, 364, 376, and 378 described above included either one or two tanks, in other embodiments the control systems may control mixing parameters of more than two tanks connected in series. In other embodiments, one or more sensors may be employed selected from the $\rho_{12}$ sensor 114, the $\rho_s$ sensor 116, the $h_1$ sensor 110, the $h_2$ sensor 112, and a flow rate sensor. Embodiments may use a mixture of sensors with no height observer 270 or density observer 290. Other embodiments may use one or more sensors with one or more height observers 270 and/or density observers 290. While the height observer 270 and the density observer 290 are discussed above, the observer concept may be extended to other sensors to reduce noise output from these and other sensors and to obtain the benefits associated with decoupling or removing disturbances and estimating intermediate rate terms. One skilled in the art will readily appreciate that coupling among control components may be altered to simplify processing, as for example combining two summation components in series by directing all the inputs to the two summation components to a single summation component or by replacing two components that calculate the same value by one component and routing the output of the one component to two destinations. Alternately, in an embodiment, a summation component summing more than two inputs may be expanded into a series of two or more summation components that collectively sum the several inputs.

Figure 13:
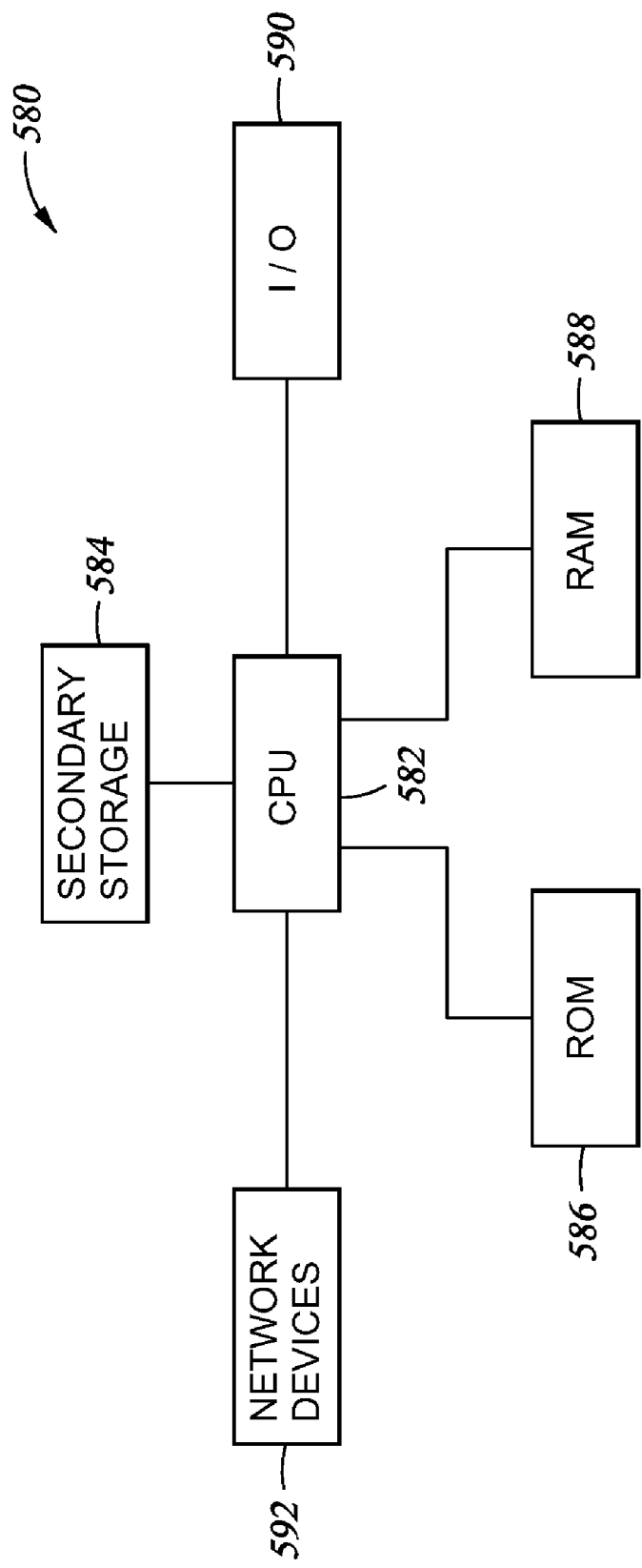
FIG. 13 illustrates one example of a general purpose computer system suitable for implementing the several embodiments of the control system and its various components.

The controller 102 used in the various control systems 100, 364, 376, and 378 described above may be implemented on any general-purpose computer with sufficient processing power, memory resources, and network throughput capability to handle the necessary workload placed upon it. FIG. 13 illustrates a typical, general-purpose computer system 580 suitable for implementing one or more embodiments of the several control system embodiments disclosed herein. The computer system 580 includes a processor 582 (which may be referred to as a central processor unit or CPU) in communication with memory devices including secondary storage 584, read only memory (ROM) 586, random access memory (RAM) 588, input/output (I/O) 590 devices, and network connectivity devices 592. The processor may be implemented as one or more CPU chips. The commands or signals output to the first actuator 18 and the second actuator 20 may be converted from a digital to an analog signal by a digital to analog converter (DAC), not shown, or otherwise conditioned to make the actuator signal conformable to a control input to the first actuator 18 and a control input to the second actuator 20.

The secondary storage 584 typically comprises one or more disk drives or tape drives and is used for non-volatile storage of data and as an over-flow data storage device if RAM 588 is not large enough to hold all working data. Secondary storage 584 may be used to store programs that are loaded into RAM 588 when such programs are selected for execution. The ROM 586 is used to store instructions and perhaps data that are read during program execution. ROM 586 is a non-volatile memory device which typically has a small memory capacity relative to the larger memory capacity of secondary storage 584. The RAM 588 is used to store volatile data and perhaps to store instructions. Access to both ROM 586 and RAM 588 is typically faster than to secondary storage 584.

I/O devices 590 may include printers, video monitors, liquid crystal displays (LCDs), touch screen displays, keyboards, keypads, switches, dials, mice, track balls, voice recognizers, card readers, paper tape readers, or other well-known input devices. The network connectivity devices 592 may take the form of modems, modem banks, ethernet cards, universal serial bus (USB) interface cards, serial interfaces, token ring cards, fiber distributed data interface (FDDI) cards, wireless local area network (WLAN) cards, radio transceiver cards such as Global System for Mobile Communications (GSM) radio transceiver cards, and other well-known network devices. These network connectivity devices 592 may enable the CPU 582 to communicate with an Internet or one or more intranets. With such a network connection, it is contemplated that the CPU 582 might receive information from the network, or might output information to the network in the course of performing the above-described method steps. Such information, which is often represented as a sequence of instructions to be executed using processor 582, may be received from and outputted to the network, for example, in the form of a computer data signal embodied in a carrier wave.

Such information, which may include data or instructions to be executed using processor 582 for example, may be received from and outputted to the network, for example, in the form of a computer data baseband signal or signal embodied in a carrier wave. The baseband signal or signal embodied in the carrier wave generated by the network connectivity devices 592 may propagate in or on the surface of electrical conductors, in coaxial cables, in waveguides, in optical media, for example optical fiber, or in the air or free space. The information contained in the baseband signal or signal embedded in the carrier wave may be ordered according to different sequences, as may be desirable for either processing or generating the information or transmitting or receiving the information. The baseband signal or signal embedded in the carrier wave, or other types of signals currently used or hereafter developed, referred to herein as the transmission medium, may be generated according to several methods well known to one skilled in the art.

The processor 582 executes instructions, codes, computer programs, scripts which it accesses from hard disk, floppy disk, optical disk (these various disk based systems may all be considered secondary storage 584), ROM 586, RAM 588, or the network connectivity devices 592.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein, but may be modified within the scope of the appended claims along with their full scope of equivalents. For example, the various elements or components may be combined or integrated in another system or certain features may be omitted, or not implemented.

Also, techniques, systems, subsystems and methods described and illustrated in the various embodiments as discrete or separate may be combined or integrated with other systems, modules, techniques, or methods without departing from the scope of the present disclosure. Other items shown or discussed as directly coupled or communicating with each other may be coupled through some interface or device, such that the items may no longer be considered directly coupled to each other but may still be indirectly coupled and in communication, whether electrically, mechanically, or otherwise with one another. Other examples of changes, substitutions, and alterations are ascertainable by one skilled in the art and could be made without departing from the spirit and scope disclosed herein.

What is claimed is:

1. A method for servicing a well bore comprising:
   connecting a mixing system to the well bore;
   controlling the mixing system to produce a material mixture with approximately a desired density;
   controlling the mixing system to provide the material mixture to the well bore at approximately a desired volumetric flow rate to service the well bore; and
   performing at least some of the controlling steps based on decoupling a negative mass flow state feedback associated with the mixing system.

2. The method of claim 1, further including inputting the desired density and the desired volumetric flow rate into a control system operable to perform the controlling steps, wherein the decoupling the negative mass flow state feedback is determined based on the product of the desired density input and the desired volumetric flow rate input.

3. The method of claim 1, further comprising:
   estimating a disturbance, wherein the controlling to produce approximately the desired density is based, at least in part, on the estimation of the disturbance.

4. The method of claim 3, wherein the estimation of the disturbance accounts for the discrepancies between the desired density and the produced density of the material mixture, discrepancies between the desired volumetric flow rate and the produced volumetric flow rate of the material mixture, inaccuracies of estimates of system parameters, and at least some unmeasured quantities associated with the mixing system.

5. The method of claim 1, further comprising:
producing a density estimate based on a sensed value of density; and
performing the controlling steps based, at least in part, on the density estimate.

6. The method of claim 5, wherein the density estimate is at least sometimes different than the sensed value of density.

7. The method of claim 5, wherein the density estimate is determined based on the sensed value of density and based on a commanded mass flow rate.

8. The method of claim 7, wherein the density estimate is determined as the superposition of a substantially zero time lagged signal based on the commanded mass flow rate and a time lagged signal based on filtering the sensed value of density.

9. The method of claim 5, wherein the producing the density estimate is based on delaying the sensed value of density.

10. The method of claim 1, wherein the controlling to produce approximately the desired density is independent from the controlling to provide approximately the desired volumetric flow rate.

11. The method of claim 10, further including performing at least some of the controlling steps based on a sensed value of density.

12. A method for servicing a well bore comprising:
connecting a mixing system to the well bore;
controlling the mixing system to produce a material mixture with approximately a desired density;
estimating a disturbance, wherein the controlling to produce approximately the desired density is based, at least in part, on the estimation of the disturbance;
controlling the mixing system to provide the material mixture to the well bore at approximately a desired volumetric flow rate to service the well bore;
processing an error term with a proportional integral function, wherein the error term is determined as the difference between a commanded input value and a corresponding sensed parameter value;
summing a command feed forward term with the result of processing the error term with the proportional integral function to produce an intermediate commanded parameter value; and
performing at least some of the controlling steps based on the intermediate commanded parameter value.

13. The method of claim 12, wherein the controlling to produce approximately the desired density is independent from the controlling to provide approximately the desired volumetric flow rate.

14. The method of claim 12, wherein the error term is determined as the difference between a commanded height of the material mixture in a tub and a sensed height of the material mixture in the tub and wherein the command feed forward term is a commanded volumetric flow rate.

15. The method of claim 12, wherein the error term is determined as the difference between a commanded density of the material mixture and a sensed density of the material mixture and wherein the command feed forward term is a commanded mass flow rate.

16. A method for servicing a well bore comprising:
connecting a mixing system to the well bore;
controlling the mixing system to produce a material mixture with approximately a desired density;
controlling the mixing system to provide the material mixture to the well bore at approximately a desired volumetric flow rate to service the well bore;
processing an error term with a proportional integral function, wherein the error term is determined as the difference between a commanded input value and a corresponding sensed parameter value;
summing a command feed forward term with the result of processing the error term with the proportional integral function to produce an intermediate commanded parameter value; and
performing at least some of the controlling steps based on the intermediate commanded parameter value, wherein at least some of the controlling steps are based on decoupling a negative mass flow state feedback associated with the mixing system.

17. A method for servicing a well bore comprising:
connecting a mixing system to the well bore;
estimating a disturbance;
controlling the mixing system to produce a material mixture with approximately a desired density based, at least in part, on the estimation of the disturbance;
controlling the mixing system to provide the material mixture to the well bore at approximately a desired volumetric flow rate to service the well bore; and
performing at least some of the controlling steps based on decoupling a negative mass flow state feedback associated with the mixing system.

18. The method of claim 17, wherein the estimation of the disturbance accounts for at least one of a discrepancy between the desired density and the produced density of the material mixture, a discrepancy between the desired volumetric flow rate and the produced volumetric flow rate of the material mixture, an inaccuracy of an estimate of a system parameter, and an unmeasured quantity associated with the mixing system.

19. A method for servicing a well bore comprising:
connecting a mixing system to the well bore;
estimating a disturbance;
controlling the mixing system to produce a material mixture with approximately a desired density based, at least in part, on the estimation of the disturbance;
controlling the mixing system to provide the material mixture to the well bore at approximately a desired volumetric flow rate to service the well bore; and
performing at least some of the controlling steps based on a command feed forward to reduce time lag in controlling the mixing system.

20. A method for servicing a well bore comprising:
connecting a mixing system to the well bore;
estimating a disturbance;
controlling the mixing system to produce a material mixture with approximately a desired density based, at least in part, on the estimation of the disturbance;
controlling the mixing system to provide the material mixture to the well bore at approximately a desired volumetric flow rate to service the well bore; and
feeding back a delayed sensed value of density to improve the accuracy of the controlling to produce approximately the desired density.

21. The method of claim 20, wherein the controlling to produce approximately the desired density is independent from the controlling to provide approximately the desired volumetric flow rate.

22. A method for servicing a well bore comprising:
connecting a mixing system to the well bore;
producing a disturbance estimate;
producing a command feed forward term;
controlling the mixing system to produce a material mixture with approximately a desired density;
controlling the mixing system to provide the material mixture to the well bore at approximately a desired volumetric flow rate to service the well bore, wherein the controlling to produce approximately the desired density is independent from the controlling to provide approximately the desired volumetric flow rate;

performing the controlling steps, at least in part, based on decoupling a negative mass flow state feedback associated with the mixing system, based on the disturbance estimate, based on the command feed forward term, and based on a density estimate, wherein the density estimate is based on a sensed density; and feeding back a time delayed sensed value of density to improve the accuracy of the controlling to produce approximately the desired density.

23. A method for servicing a well bore comprising:
connecting a mixing system to the well bore;
controlling the mixing system to produce a material mixture with approximately a desired density;
controlling the mixing system to provide the material mixture to the well bore at approximately a desired volumetric flow rate to service the well bore; and
estimating a disturbance, wherein (i) controlling the mixing system to produce a material mixture with approximately a desired density, (ii) controlling the mixing system to provide the material mixture to the well bore at approximately a desired volumetric flow rate to service the well bore, or both (i) and (ii) is based, at least in part, on the estimation of the disturbance.

24. The method of claim 23, wherein the estimation of the disturbance accounts for at least one of a discrepancy between the desired density and the produced density of the material mixture, a discrepancy between the desired volumetric flow rate and the produced volumetric flow rate of the material mixture, an inaccuracy of an estimate of a system parameter, and an unmeasured quantity associated with the mixing system.

25. The method of claim 23, wherein the controlling the mixing system based, at least in part, on the estimation of the disturbance comprises decoupling the disturbance.

26. The method of claim 23, further including performing at least some of the controlling steps based on decoupling a negative mass flow state feedback associated with the mixing system.

27. The method of claim 23, further including performing at least some of the controlling steps based on a command feed forward.

28. The method of claim 23, further including performing at least some of the controlling steps based on a density estimate, wherein the density estimate is based on a sensed density of the material mixture conditioned by proportional and integral (PI) processing and based on a mass flow rate feed forward term.

* * * * *